(12) United States Patent
Li et al.

(10) Patent No.: US 11,464,795 B2
(45) Date of Patent: Oct. 11, 2022

(54) SAPONIN COMPOUND TARGETING PD-1 AND APPLICATION THEREOF

(71) Applicants: EAST CHINA UNIVERSITY OF SCIENCE AND TECHNOLOGY, Shanghai (CN); YUNNAN UNIVERSITY, Kunming (CN); SHANGHAI INSTITUTE OF MATERIA MEDICA, CHINESE ACADEMY OF SCIENCES, Shanghai (CN)

(72) Inventors: Honglin Li, Shanghai (CN); Weilie Xiao, Kunming (CN); Lili Zhu, Shanghai (CN); Lina Quan, Shanghai (CN); Qiao Li, Shanghai (CN); Yanyan Diao, Shanghai (CN); Zhenjiang Zhao, Shanghai (CN); Hualiang Jiang, Shanghai (CN)

(73) Assignees: East China University Of Science And Technology, Shanghai (CN); Yunnan University, Kunming (CN); Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/630,309

(22) PCT Filed: Jul. 12, 2018

(86) PCT No.: PCT/CN2018/095426
§ 371 (c)(1),
(2) Date: Jan. 10, 2020

(87) PCT Pub. No.: WO2019/011293
PCT Pub. Date: Jan. 17, 2019

(65) Prior Publication Data
US 2020/0163983 A1 May 28, 2020

(30) Foreign Application Priority Data
Jul. 13, 2017 (CN) .......................... 201710570889.0

(51) Int. Cl.
*A61K 31/704* (2006.01)
*A61P 35/00* (2006.01)
*A61K 31/56* (2006.01)

(52) U.S. Cl.
CPC ............ *A61K 31/704* (2013.01); *A61K 31/56* (2013.01); *A61P 35/00* (2018.01)

(58) Field of Classification Search
None
See application file for complete search history.

(56) References Cited

U.S. PATENT DOCUMENTS

2003/0108628 A1* 6/2003 Babish .................. A61K 36/00
424/756

FOREIGN PATENT DOCUMENTS

| CN | 102657660 A | 9/2012 |
|----|-------------|--------|
| CN | 105769889 A | 6/2016 |
| CN | 105998032 A | 10/2016 |

(Continued)

OTHER PUBLICATIONS

Zarganes-Tzitzikas, T., Konstantinidou, M., Gao, Y., Krzemien, D., Zak, K., Dubin, G., . . . & Dömling, A. (2016). Inhibitors of programmed cell death 1 (PD-1): a patent review (2010-2015). Expert opinion on therapeutic patents, 26(9), 973-977. (Year: 2016).*
Gong, J., Chehrazi-Raffle, A., Reddi, S., & Salgia, R. (2018). Development of PD-1 and PD-L1 inhibitors as a form of cancer immunotherapy: a comprehensive review of registration trials and future considerations. Journal for immunotherapy of cancer, 6(1), 1-18. (Year: 2018).*

(Continued)

*Primary Examiner* — Dale R Miller
(74) *Attorney, Agent, or Firm* — Mintz, Levin, Cohn, Ferris, Glovsky and Popeo, P.C.

(57) ABSTRACT

Provided are use of a saponin compound of formula (I) or (II), or a pharmaceutically acceptable salt, prodrug or solvate thereof, in the manufacture of a medicament targeting PD-1. The medicament targeting PD-1 is one which treats a disease by inhibiting PD-1 from binding to a ligand thereof. The disease may be a tumor, an infection caused by a bacterium, a virus or a fungus, or an inflammatory disease.

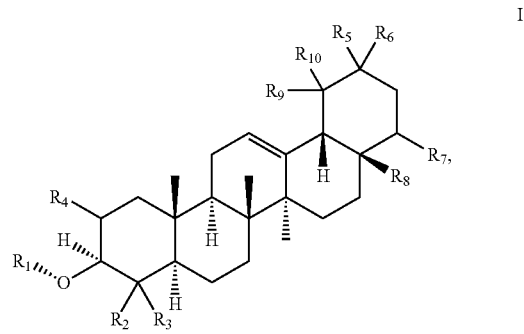

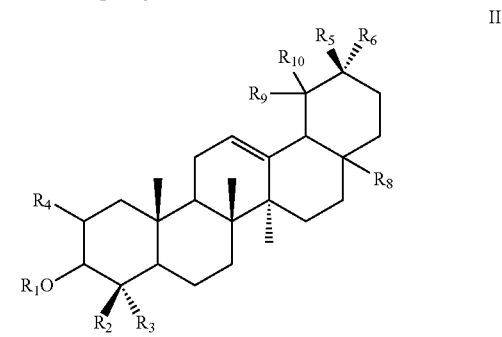

2 Claims, 16 Drawing Sheets

(56) References Cited

FOREIGN PATENT DOCUMENTS

| | | |
|---|---|---|
| CN | 105998033 A | 10/2016 |
| CN | 106038571 A | 10/2016 |
| CN | 106581006 A | 4/2017 |
| CN | 106619816 A | 5/2017 |
| CN | 106727854 A | 5/2017 |
| CN | 106749488 A | 5/2017 |
| CN | 106822206 A | 6/2017 |
| JP | H045235 A | 1/1992 |
| KR | 20030092170 A | 12/2003 |
| WO | 2015/171598 A1 | 11/2015 |

OTHER PUBLICATIONS

Skalniak, L., Zak, K. M., Guzik, K., Magiera, K., Musielak, B., Pachota, M., . . . & Holak, T. A. (2017). Small-molecule inhibitors of PD-1/PD-L1 immune checkpoint alleviate the PD-L1-induced exhaustion of T-cells. Oncotarget, 8(42), 72167. (Year: 2017).*

English Translation of the International Search Report corresponding to PCT/CN2018/095426 dated Sep. 27, 2018; 4 pages.

Jang, Won-Jun et al., "SB365 *Pulsatilla* saponin D, suppresses the growth of gefitinib-resistant NSCLC cells with Met amplification," *Oncology Reports* (Dec. 31, 2014) 32:2612-2618.

Li, Sainan et al., "Extraction and in vitro screening of potential acetylcholinesterase inhibitors from the leaves of *Panax japonicas*," *Journal of Chromatography B*; Accepted manuscript (Jul. 12, 2017) vol. 1061-1062; pp. 139-145 (submission is 23 pages).

Shin, Y. K. et al., "Macelignan inhibits bee pathogenic fungi *Ascophaera apis* growth through HOG1 pathway," *Brazilian Journal of Medical and Biological Research* (Dec. 31, 2016) 49(7):e5313, pp. 1-9.

Singh, Thakur Rohit et al., "Study of hypoglycemic effect of corosolic acid & its comparative evaluation with standard drug glibenclamide in alloxan induced diabetes in female albino mice," *The Pharma Innovation Journal* (Dec. 31, 2016) 5(10):56-59.

First Examination Report dated Nov. 19, 2021 corresponding to GB2000501.3; 6 pages.

Second Examination Report dated Feb. 4, 2022 corresponding to GB2000501.3; 2 pages.

Avato et al., "Antimicrobial Activity of Saponins from *Medicago* sp.:Structure-Activity Relationship," Phytotherapy Research, 20, 454-457, 2006, 5 pages.

Choi et al., "Anti-Rheumatoid Arthritis Effect of the Kochia scoparia Fruits and Activity Comparison of Momordin Ic, its Prosapogenin and Sapogenin," Archives of Pharmacal Research, vol. 25, No. 3, 336-342, Mar. 5, 2002, 8 pages.

Kashyap et al., "Ursolic Acid and Oleanolic Acid: Pentacycluc Terpenoids with Promising Anti-Inflammatory Activities," Recent Patents on Inglammation & Allergy Drug Discovery, vol. 10, No. 1, Jul. 3, 2016, 15 pages.

Kim et al., "Hederagenin Supplementation Alleviates the Pro-Inflammatory and Apoptotic Response to Alcohol in Rats," Nutrients, 9, 41, Jan. 6, 2017, 14 pages.

Kong et al., "Oleanolic acid and ursolic acid: Novel hepatitis C virus antivirals that inhibit NS5B activity," Antiviral Research, 98, 2013, 44-53.

Liu et al., "Hederagenin from the leaves of ivy (Hedera helix L.) induces apoptosis in human LoVo colon cells through the mitochondrial pathway," Bio Med Central Complementary and Alternative Medicine, 14:412, 2014, 11 pages.

Lucio et al., "Oleanolic Acid Initiates Apoptosis in Non-Small Cell Lung Cancer Cell Lines and Reduces Metastasis of a B16F10 Melanoma Model In Vivo," PLoS One, e28596, vol. 6, Issue 12, Dec. 2011, 11 pages.

Luo et al., "Triterpenoid saponins of Sanguisorba Officinalis and their anti-inflammatory activity," Chinese Journal of Medicinal Chemistry, vol. 18, No. 2, School of Traditional Chinese Materia Medica, Shanyang Pharmaceutical University, Shenyang 110016, China, Apr. 2008, 138-141, 5 pages.

Reyes-Zurita et al., "The natural triterpene maslinic acid induces apoptosis in HT29 colon cancer cells by a JNK-p53-dependent mechanism," BioMed Central Cancer, 11:154, 2011.

Ryu et al., "Antiviral Activity of Triterpenoid Derivatives," Archives of Pharmacal Research, vol. 16, No. 4, 1993, 339-342, 5 pages.

Wu et al., "Momordin Ic, a new natural SENP1 inhibitor, inhibits prostate cancer cell proliferation," Oncotarget, vol. 7, No. 37, 58995-59005, Jul. 16, 2016, 12 pages.

Yanaki et al., "In Vivo Antitumor Effects of MK615 Led by PD-LI Downregulation," Integrative Cance Therapies, vol. 17(3), 2018, 646-653, 10 pages.

Zhu et al., "Ziyuglycoside II induces cell cycle arrest and apoptosis through activation of ROS/JNK pathway in human breast cancer cells," Key Laboratory of Nuclear Medicine, Ministry of Health, Jiangsu Key Laboratory of Molecular Nuclear Medicine, Jiangsu Institute of Nuclear Medicine, Wuxi 214063, Jiangsu Province, China Toxicology Letters 227 (2014) 65-73, 10 pages.

* cited by examiner

SAPONIN COMPOUND TARGETING PD-1 AND APPLICATION THEREOF

TECHNICAL FIELD

The present invention relates to the field of medicinal chemistry; and in particular, to saponin compounds targeting PD-1, especially hPD-1, and uses thereof for preparing a medicament for treating tumors, infections caused by bacteria, viruses or fungi, or inflammatory diseases.

BACKGROUND

Currently, immunotherapy is a popular method for treating cancer. Compared with traditional methods, such as surgical resection, radiation therapy and chemotherapy, immunotherapy has advantages, such as safety, effectiveness and low toxicity. Blocking immune checkpoints by using blocking agents is a relatively effective method in immunotherapy. Programmed death receptor 1 (PD-1) is one of deeply studied immune checkpoints. A cancer can be treated by blocking the interaction between PD-1 and a receptor thereof, PD-L1 or PD-L2. It is currently a hot spot in the research on blocking agents targeting PD-1 or a receptor thereof.

Therefore, there are important clinical significance and application prospects for the research and development of small molecule inhibitors as candidates to block PD-1/PD-L1 interaction.

SUMMARY OF THE INVENTION

The object of the present invention is to provide a small molecule inhibitor for blocking PD-1/PD-L1 interaction, so that it can be used as a medicament for treating tumors, infections caused by bacteria, viruses or fungi or inflammatory diseases.

In a first aspect, a use of a saponin compound represented by Formula I or II or a pharmaceutically acceptable salt, prodrug, or solvate thereof in the preparation of a medicament targeting PD-1, is provided in the present invention, wherein,

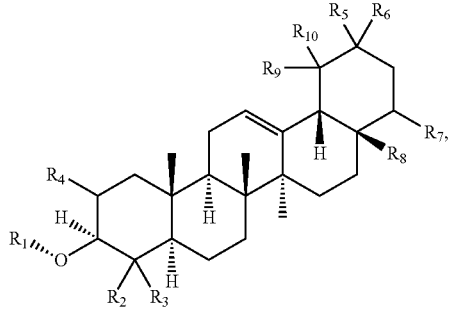

I

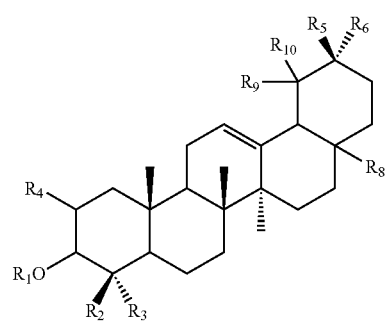

II $R_1$ is selected form the group consisting of:

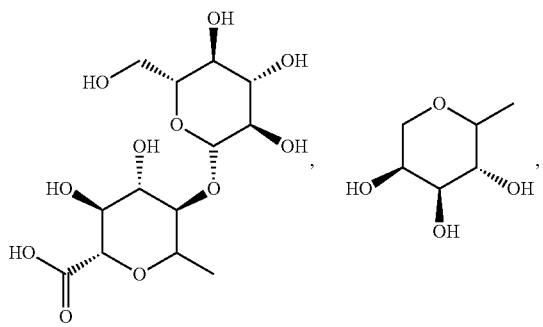

H,

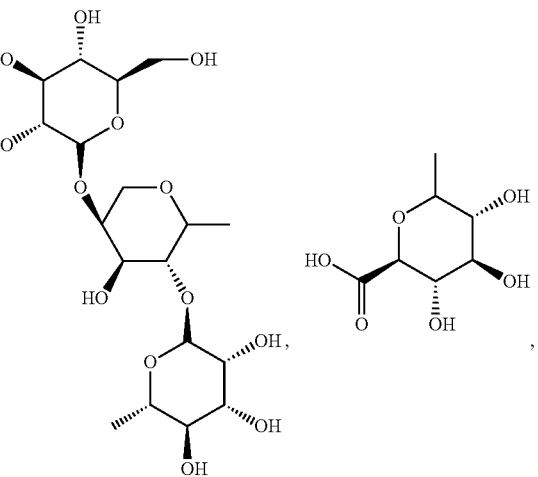

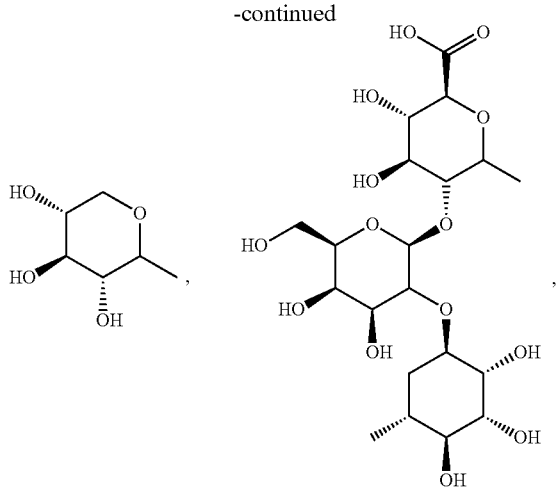

R₂ and R₃ are each independently selected from the group consisting of: H, a substituted or unsubstituted $C_{1-6}$ alkyl, OH, substituted or unsubstituted $C_{1-6}$ alkylenehydroxy;

R₄ is selected from the group consisting of: H, OH, a substituted or unsubstituted $C_{1-6}$ alkoxy, —OC(O)R₁₁, wherein R₁₁ is selected from hydrogen or a substituted or unsubstituted $C_{1-6}$ alkyl, preferably H or a substituted or unsubstituted $C_{1-3}$ alkyl;

R₅ and R₆ are each independently selected from the group consisting of: H, a substituted or unsubstituted $C_{1-6}$ alkyl;

R₇ is selected from the group consisting of: H, OH;

R₈ is selected from the group consisting of: H, a $C_{1-3}$ carboxyl, substituted or unsubstituted $C_{2-7}$ ester group,

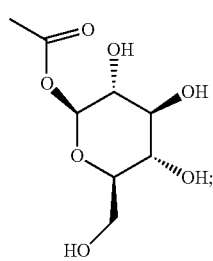

R₉ and R₁₀ are each independently selected from the group consisting of: H, a substituted or unsubstituted $C_{1-6}$ alkyl, OH.

In a preferred embodiment, the PD-1 is human PD-1, i.e., hPD-1.

In a specific embodiment, in the compound of Formula I, R₂ and R₃ are each independently selected from a group consisting of: H, a substituted or unsubstituted $C_{1-3}$ alkyl, OH, substituted or unsubstituted $C_{1-3}$ alkylenehydroxyl;

R₅ and R₆ are each independently selected from a group consisting of: H, a substituted or unsubstituted $C_{1-3}$ alkyl;

R₈ is selected from the group consisting of: H, —COOH,

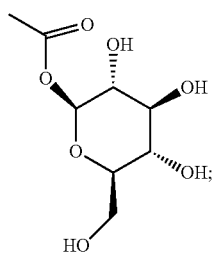

R₉ and R₁₀ are each independently selected from the group consisting of: H, a substituted or unsubstituted $C_{1-3}$ alkyl, OH;

R₁, R₄ and R₇ are as described above.

In a specific embodiment, the compound of Formula II is a compound of the following formula,

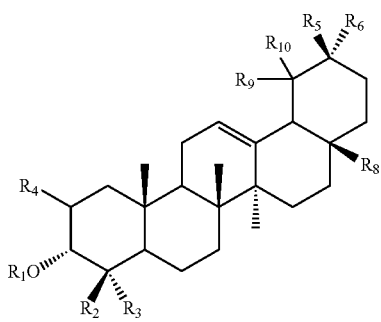

R₁, R₂, R₃, R₄, R₅, R₆, R₇, R₈, R₉ and R₁₀ are defined as described above.

In a specific embodiment, the compound of Formula I or II is selected from the group consisting of:

| No. | Structure |
| --- | --- |
| 1 | ![structure] |

-continued
| No. | Structure |
|---|---|
| 2 | 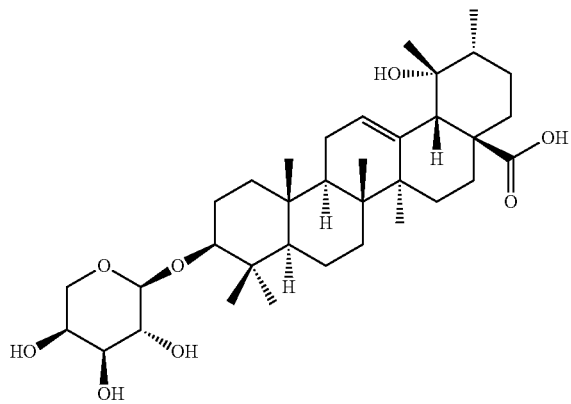 |
| 3 | 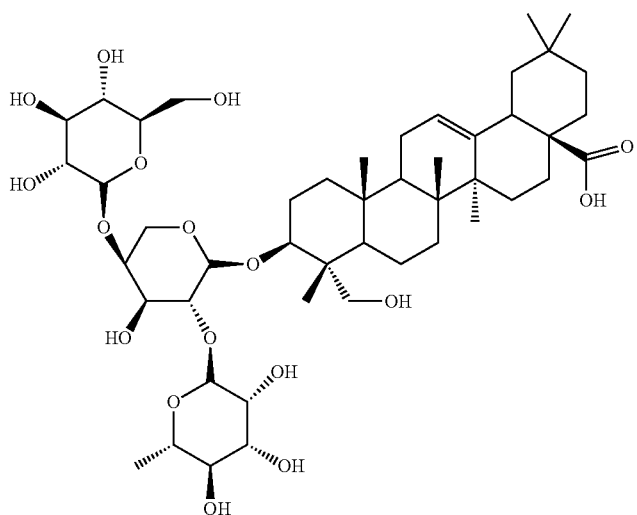 |
| 4 | 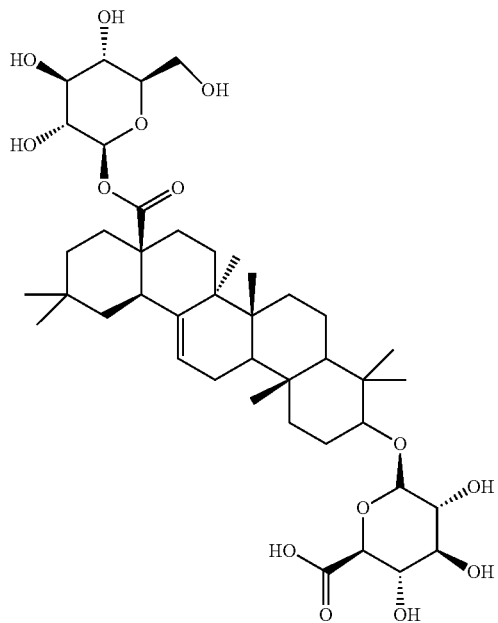 |

-continued

| No. | Structure |
|---|---|
| 5 | 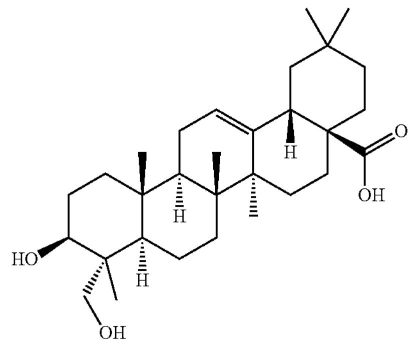 |
| 6 | 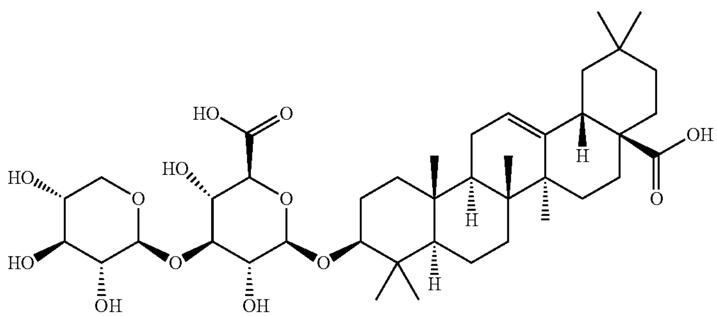 |
| 7 | 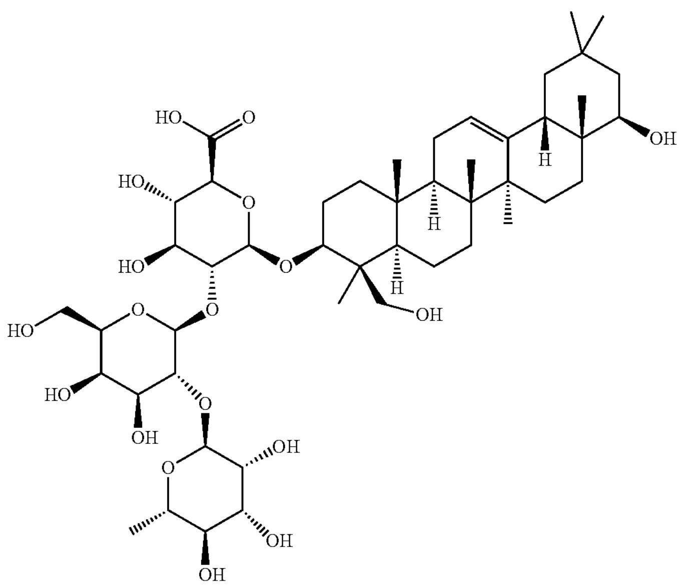 |
| 8 | 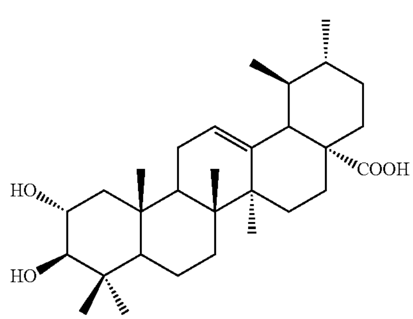 |

-continued
| No. | Structure |
|---|---|
| 9. | 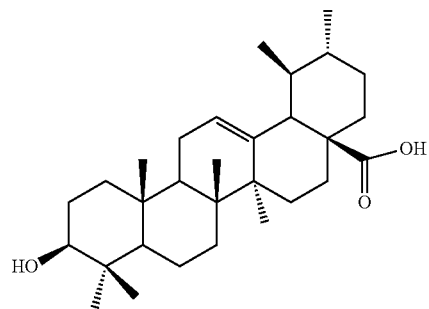<br>Ursolic acid (UA, 2) |
| 10. | 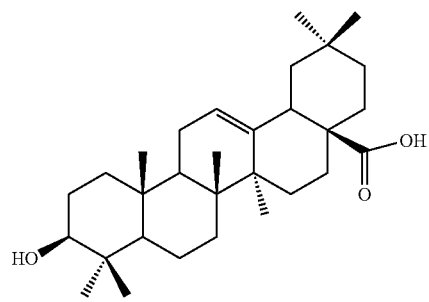<br>Oleanolic acid (OA, 1) |
| 11 | 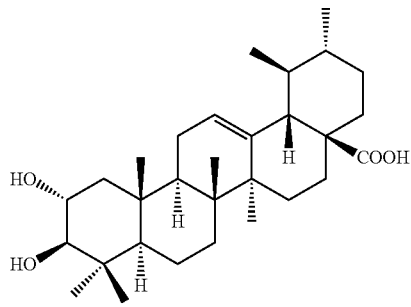 |
| 12 | 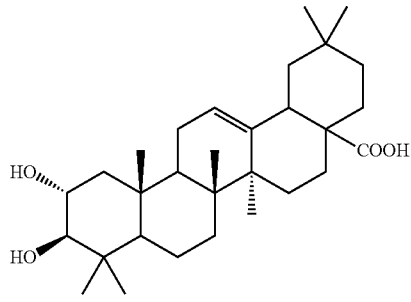 |

-continued

| No. | Structure |
|---|---|
| 13 | (chemical structure of a pentacyclic triterpenoid with two OH groups, one COOH group, and a C=C double bond) |

In a specific embodiment, the medicament targeting PD-1 is a medicament that treats a disease by inhibiting PD-1 from binding to its ligand.

In a specific embodiment, the disease is a tumor, an infection caused by bacteria, virus or fungus, or an inflammatory disease.

In a specific embodiment, the tumor includes, but not limited to, melanoma, lung cancer, kidney cancer, ovarian cancer, prostate cancer, breast cancer, colon cancer, bone cancer, pancreatic cancer, skin cancer, head and neck cancer, uterine cancer, rectal cancer, anal cancer, gastric cancer, testicular cancer, carcinoma of fallopian tube, endometrial cancer, cervical cancer, vaginal cancer, vulvar cancer, Hodgkin's disease, non-Hodgkin's lymphoma, esophageal cancer, small bowel cancer, endocrine system cancer, thyroid cancer, parathyroid cancer, adrenal cancer, soft tissue sarcoma, urethral cancer, penile cancer, acute myeloid leukemia, chronic myeloid leukemia, acute lymphocytic leukemia, chronic lymphocytic leukemia, pediatric solid tumors, lymphocytic lymphoma, bladder cancer, kidney or ureter cancer, renal pelvis cancer, central nervous system (CNS) tumor, primary CNS lymphoma, spinal axoma, brainstem glioma, pituitary adenoma, Kaposi's sarcoma, epidermoid carcinoma, squamous cell carcinoma, T cell lymphoma;

The viruses include, but not limited to: hepatitis virus, varicella virus, influenza virus, adenovirus, coronavirus, measles virus, dengue virus, polio virus, rabies virus;

The bacteria include, but not limited to, *chlamydia, rickettsia*, mycobacteria, *staphylococcus*, pneumococcus, *Vibrio cholerae, Clostridium* tetanus;

The fungi include, but not limited to: *Candida, Aspergillus, S. dermatitis;*

The inflammatory diseases include, but not limited to, ankylosing spondylitis, autoimmune hemolytic anemia, arthritis, myasthenia gravis, systemic lupus erythematosus, rheumatoid arthritis, malignant anemia, polymyositis.

In a specific embodiment, the lung cancer is non-small cell lung cancer; and the hepatitis virus is hepatitis A, B, or C virus.

In a second aspect, a method for inhibiting PD-1 from binding PD-L1 is provided in the present invention, comprising the steps of using the compound of the first aspect of the present invention or a pharmaceutically acceptable salt, prodrug, solvate thereof, or a pharmaceutical composition comprising said compound to inhibit PD-1 from binding to PD-L1.

In a preferred embodiment, the method is used for non-therapeutic purposes.

In a third aspect, a pharmaceutical composition is provided in the present invention, comprising the compound of the first aspect of the present invention or a pharmaceutically acceptable salt, prodrug, solvate thereof, and a pharmaceutically acceptable excipient.

It should be understood that, within the scope of the present invention, the above technical features of the present invention and the technical features specifically described in the following (such as in the Examples) can be combined with each other to form a new or preferred technical solution, which will not be described one by one herein.

MODES FOR CARRYING OUT THE INVENTION

Figure 1:
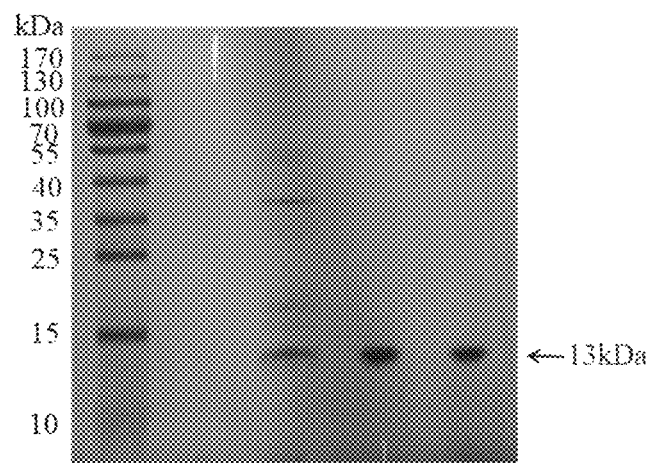
FIG. 1 shows the results of 14% SDS-PAGE gel electrophoresis of the purified PD-1 recombinant protein from Example 2. The molecular weight of the target band is about 13 kDa, which is consistent with the theoretical molecular weight.

After extensive and intensive research, the inventors unexpectedly discovered a series of structurally similar saponin compounds which can target PD-1, block the interaction between PD-1 and a receptor thereof, and then be used to treat tumors, infections caused by a bacteria, virus or fungus, or inflammatory diseases. The present invention has been completed based on the above findings.

PD-1

PD-1 is an important immunosuppressive receptor on the surface of T cells, which is a transmembrane glycoprotein of type I immunoglobulin superfamily consisting of 288 amino acids. It was originally obtained from hybridomas in an apoptotic state and clones of hematopoietic progenitor cell lines in mice by subtractive hybridization, considered to be associated with apoptosis and thus named as programmed death-1 (PD-1). PD-1 protein is induced to be up-regulated mainly in T cells, B cells, and NK cells. PD-L1 and PD-L2 are two endogenous ligands of PD-1. PD-L1 is expressed in activated T cells, B cells, monocytes and many types of tumor cells, while PD-L2 is mainly expressed on activated macrophages, dendritic cells, bone marrow-derived stromal cells, and certain tumor cells. Therefore, PD-L1 is *populus* as compared with PD-L2. Studies have shown that the interaction between PD-1 on activated T cells and its ligand can significantly inhibit biological functions of effector T cells, thereby resulting in immune escape of some tumors, autoimmune diseases, viral infectious diseases, and the like. There is a good application prospect for blocking the interaction between PD-1 and PD-L1/PD-L2.

At present, antibodies against PD-1 and PD-L1 pathways are mainly divided into two types: 1. binding PD-1, thereby blocking the interaction between PD-1 and PD-L1; 2. binding PD-L1, thereby blocking interaction between PD-1 and PD-L1. Main representatives of antibodies binding PD-1 are Nivolumab and Pembrolizumab; and main representatives of antibodies binding PD-L1 are BMS-936559 and MPDL3280A. However, such macromolecular antibody drugs have disadvantages, such as high production cost and immunogenicity. Therefore, there is a good application prospect for small-molecule drug which is of low production cost, less prone to immunogenicity, easy to penetrate tissues, and has better stability.

In a specific embodiment, the PD-1 of the present invention is human PD-1, i.e., hPD-1.

Saponin Compounds of the Present Invention

Some groups involved herein are defined as follows:

As used herein, "alkyl" refers to a lower alkyl, that is, a saturated branched or straight chain alkyl having a carbon chain of 1-6 carbon atoms in length. Examples of alkyl include, but not limited to, methyl, ethyl, n-propyl, isopropyl, n-butyl, isobutyl, hexyl, and the like. An alkyl may be substituted with one or more substituents, for example a halogen or haloalkyl. For example, the alkyl may be an alkyl substituted with 1 to 4 fluorine atoms, or the alkyl may be an alkyl substituted with a fluoroalkyl.

As used herein, when the term "substituted" is used to define or modify a group, for example, when referring to a substituted alkoxy, it means that the defined or modified group may be substituted with one or more substituents. For example, the defined or modified group is substituted with 1-6, or 1-3, or 1 substituent, as long as the number of substituents meets the valence requirement of the group. In a specific embodiment, the substituent may be, but not limited to, a halogen, lower alkyl (e.g., an alkyl of 1 to 3 carbon atoms), hydroxyl, nitro, cyano, and the like.

As used herein, "halogen" refers to fluorine, chlorine, bromine or iodine.

As used herein, "carboxy" refers to a group having the structural formula "—RCOOH", where R is a substituted or unsubstituted alkyl, such as a lower alkyl of 1 to 3 carbon atoms. In a specific embodiment, a carboxyl is COOH.

As used herein, "ester group" refers to a group represented by the structural formula "—$R_a$COOR$_b$", wherein $R_a$ is an alkyl of 0 to 3 carbon atoms, and $R_b$ is an alkyl of 1-3 carbon atoms; therefore, the ester group as described herein may be a substituted or unsubstituted ester group of 2-7 carbon atoms. In a specific embodiment, the ester group as described herein includes, but not limited to, methyl formate, ethyl formate, propyl formate, methyl acetate, ethyl acetate, propyl acetate, methyl propionate, ethyl propionate, and propyl propionate.

In a specific embodiment, the saponin compound of Formula I or II of the present invention or a pharmaceutically acceptable salt, prodrug or solvate thereof can be used to prepare a medicament targeting PD-1, wherein,

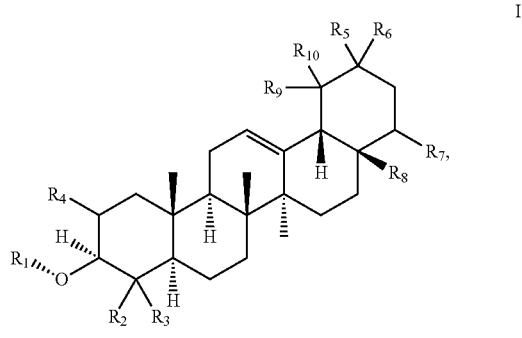

I

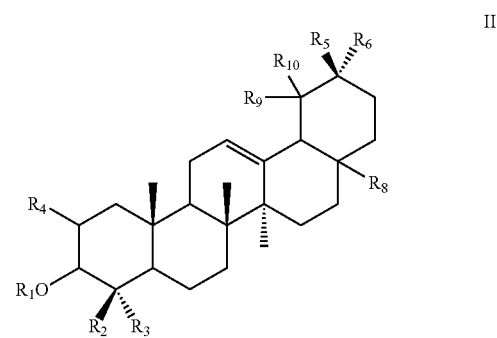

II $R_1$ is selected from the group consisting of:

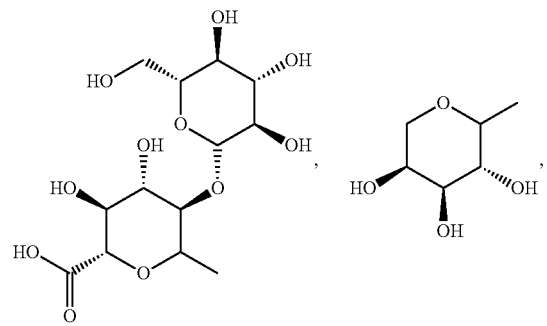

-continued

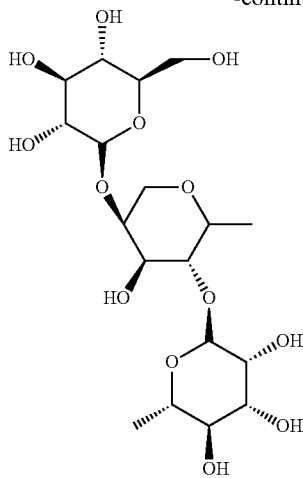

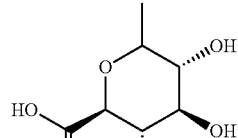

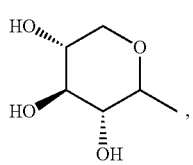

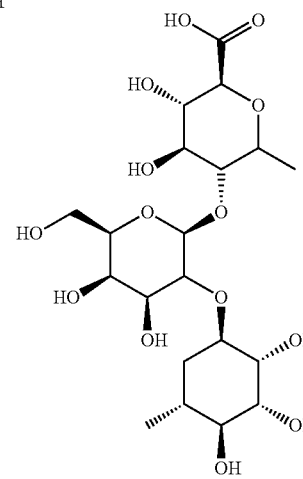

$R_2$ and $R_3$ are each independently selected from a group consisting of: H, a substituted or unsubstituted $C_{1-6}$ alkyl (preferably substituted or unsubstituted $C_{1-3}$ alkyl), OH, substituted or unsubstituted $C_{1-6}$ alkylenehydroxy (preferably substituted or unsubstituted $C_{1-3}$ alkylenehydroxy);

$R_4$ is selected from the group consisting of: H, OH, a substituted or unsubstituted $C_{1-6}$ alkoxy (preferably substituted or unsubstituted $C_{1-3}$ alkoxy), —OC(O)$R_{11}$, wherein $R_{11}$ is selected from hydrogen or a substituted or unsubstituted $C_{1-6}$ alkyl, preferably H or a substituted or unsubstituted $C_{1-3}$ alkyl;

$R_5$ and $R_6$ are each independently selected from the group consisting of: H, a substituted or unsubstituted $C_{1-6}$ alkyl (preferably substituted or unsubstituted $C_{1-3}$ alkyl);

$R_7$ is selected from the group consisting of: H, OH;

$R_8$ is selected from the group consisting of: H, a $C_{1-3}$ carboxyl, substituted or unsubstituted $C_{2-7}$ ester group,

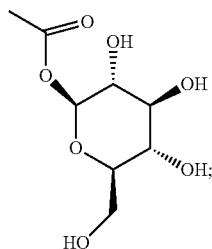

$R_9$ and $R_{10}$ are each independently selected from the group consisting of: H, a substituted or unsubstituted $C_{1-6}$ alkyl (preferably substituted or unsubstituted $C_{1-3}$ alkyl), OH.

A skilled person will know that $R_1$ and $R_8$ in the above compound of Formula II may also have a specific configuration. Therefore, in a further embodiment, the compound of Formula II is a compound of the following formula,

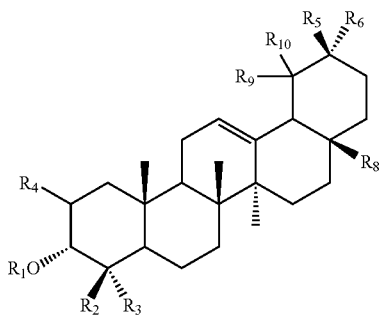

Wherein $R_1$, $R_2$, $R_3$, $R_4$, $R_5$, $R_6$, $R_7$, $R_8$, $R_9$ and $R_{10}$ are defined as described above.

For example, the saponin compound of Formula I or II of the present invention is a compound selected from the group consisting of:

| No. | Structure |
|---|---|
| 1 | ![structure 1] |

-continued
| No. | Structure |
|---|---|
| 2 | 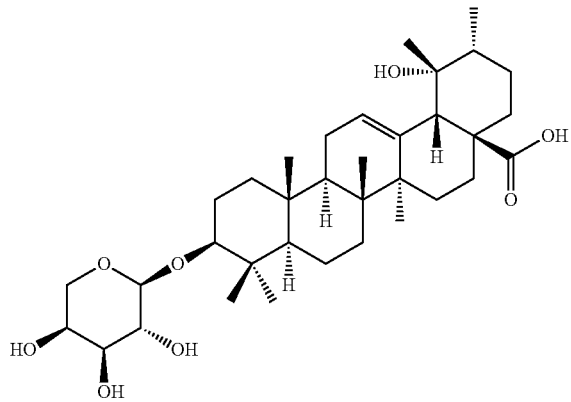 |
| 3 | 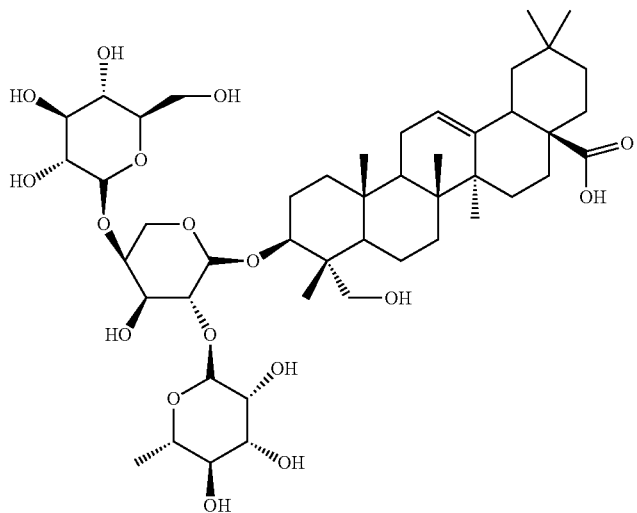 |
| 4 | 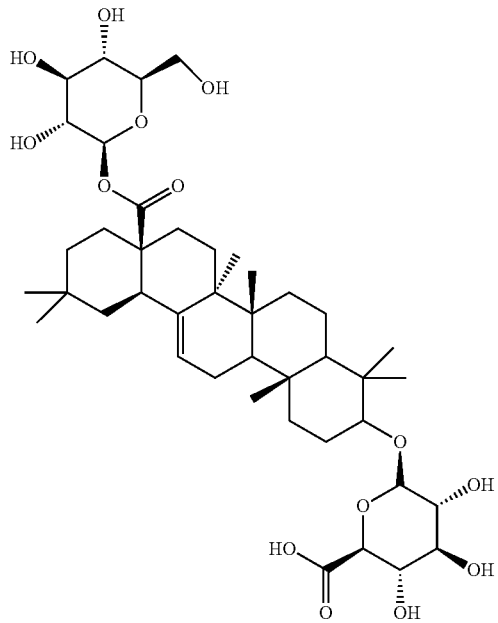 |

-continued
| No. | Structure |
|---|---|
| 5 | 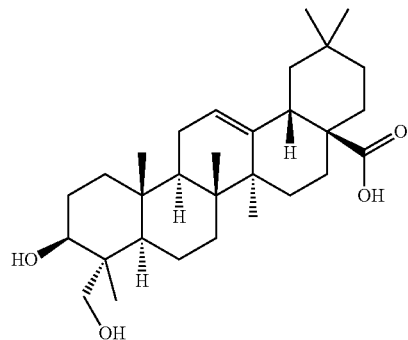 |
| 6 | 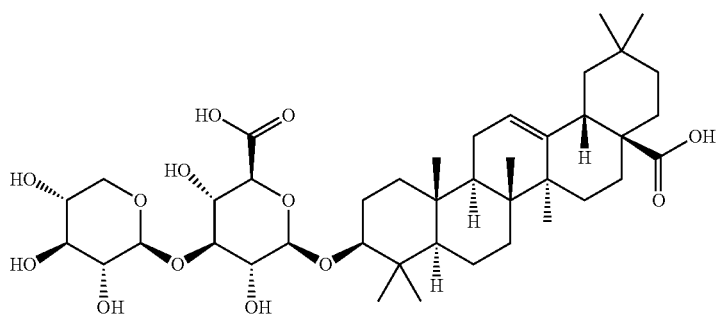 |
| 7 | 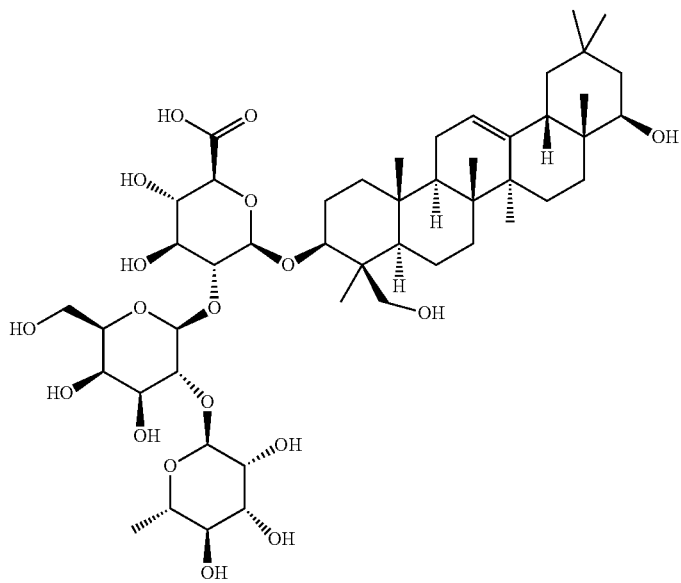 |
| 8 | 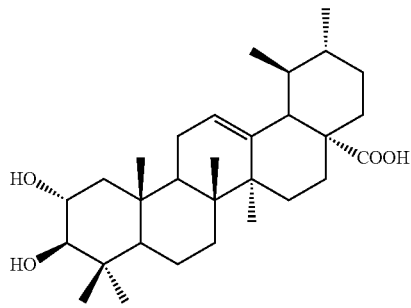 |

-continued
| No. | Structure |
|---|---|
| 9. | 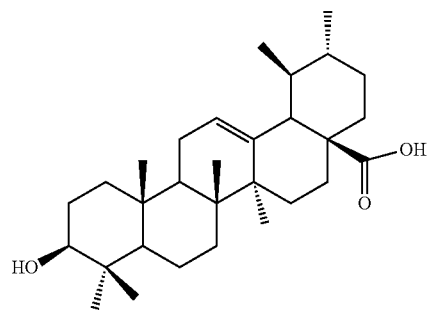<br>Ursolic acid (UA, 2) |
| 10. | 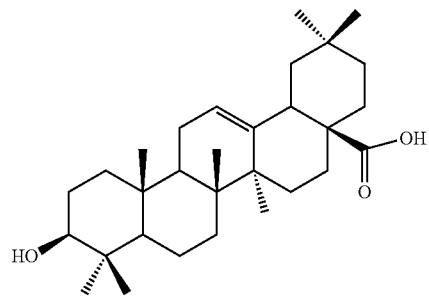<br>Oleanolic acid (OA, 1) |
| 11 | 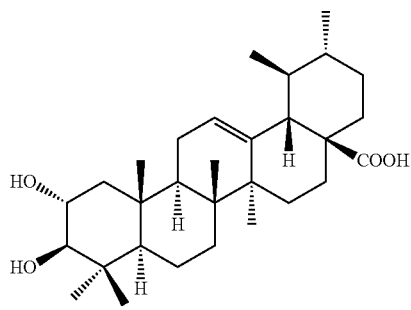 |
| 12 | 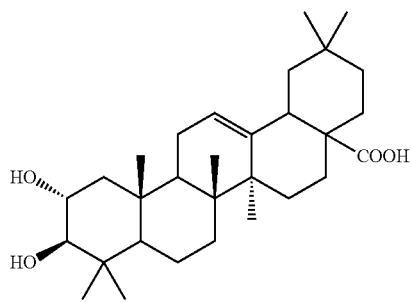 |

-continued

| No. | Structure |
|-----|-----------|
| 13  | (chemical structure) |

The compound of the present invention can treat a disease by inhibiting PD-1 from binding to its ligand. The disease may be a tumor, an infection caused by bacteria, virus or fungus, or an inflammatory disease. The tumor includes, but not limited to, melanoma, lung cancer, kidney cancer, ovarian cancer, prostate cancer, breast cancer, colon cancer, bone cancer, pancreatic cancer, skin cancer, head and neck cancer, uterine cancer, rectal cancer, anal cancer, gastric cancer, testicular cancer, carcinoma of fallopian tube, endometrial cancer, cervical cancer, vaginal cancer, vulvar cancer, Hodgkin's disease, non-Hodgkin's lymphoma, esophageal cancer, small bowel cancer, endocrine system cancer, thyroid cancer, parathyroid cancer, adrenal cancer, soft tissue sarcoma, urethral cancer, penile cancer, acute myeloid leukemia, chronic myeloid leukemia, acute lymphocytic leukemia, chronic lymphocytic leukemia, pediatric solid tumors, lymphocytic lymphoma, bladder cancer, kidney or ureter cancer, renal pelvis cancer, central nervous system (CNS) tumor, primary CNS lymphoma, spinal axoma, brainstem glioma, pituitary adenoma, Kaposi's sarcoma, epidermoid carcinoma, squamous cell carcinoma, T cell lymphoma; the viruses include, but not limited to: hepatitis virus, varicella virus, influenza virus, adenovirus, coronavirus, measles virus, dengue virus, polio virus, rabies virus; the bacteria include, but not limited to, *chlamydia, rickettsia,* mycobacteria, *staphylococcus,* pneumococcus, *Vibrio cholerae, Clostridium* tetanus; the fungi include, but not limited to: *Candida, Aspergillus, S. dermatitis*; and the inflammatory diseases include, but not limited to, ankylosing spondylitis, autoimmune hemolytic anemia, arthritis, myasthenia gravis, systemic lupus erythematosus, rheumatoid arthritis, malignant anemia, polymyositis. In a preferred embodiment, the lung cancer is non-small cell lung cancer; and the hepatitis virus is hepatitis A, B, or C virus.

Based on the above findings, a method for inhibiting the binding of PD-1 to PD-L1 by using the compound of the present invention or a pharmaceutically acceptable salt, prodrug, solvate thereof, or a pharmaceutical composition comprising said compound to inhibit PD-1 from binding to PD-L1 is also provided in the present invention. A skilled person will appreciate that the method can be used for non-therapeutic purposes, such as, but not limited to, scientific research purposes.

Examples of pharmaceutically acceptable salts of the compounds of the invention include, but not limited to, inorganic and organic acid salts, such as hydrochloride, hydrobromide, sulfate, citrate, lactate, tartrate, maleate, fumarate, mandelate, and oxalate; and inorganic and inorganic and organic base salts formed with base, such as sodium hydroxyl, tris(hydroxymethyl)aminomethane (TRIS, tromethamine), and N-methylglucamine.

A skilled person can determine the amount of the compound of the present invention to be administered, although each person's needs are different. A dosage is an amount which is effective to ameliorate or eliminate one or more conditions. For the treatment of a particular disease, an effective amount is an amount which is sufficient to ameliorate or in some way reduce symptoms associated with the disease. Such an amount may be administered as a single dosage or may be administered according to an effective treatment regimen. The dosage may cure a disease, but it is usually administered to improve symptoms of the disease. Generally, repeated administration is required to achieve the desired improvement in symptoms. The dosage of a medicament will be determined based on the patient's age, health and weight, the type of concurrent treatment, the frequency of treatment, and the required treatment benefit.

The compounds of the present invention can also be formulated into formulations suitable for a variety of routes of administration, including but not limited to those formulated for parenteral, subcutaneous, intravenous, muscular, intraperitoneal, transdermal, oral, intrathecal, intracranial, nasal or topical administration for treating tumors and other diseases.

The pharmaceutical preparation containing the compound of the present invention can be administered to any mammal as long as they can obtain the therapeutic effects of the compound of the present invention. Among these mammals, the most important is human.

Pharmaceutical formulations containing a compound of the present invention can be manufactured in a known manner, for example, manufactured by traditional processes, such as mixing, granulating, ingot-making, dissolving, or freeze-drying. When manufacturing oral preparations, solid excipients and active compounds can be combined, and the obtained mixture can be selectively ground. After adding an appropriate amount of adjuvant, the granule mixture may be processed to obtain a tablet or lozenge core, if necessary.

Suitable excipients are in particular fillers, for example, sugars such as lactose or sucrose, mannitol or sorbitol; cellulose preparations or calcium phosphates, such as tricalcium phosphate or calcium hydrogen phosphate; and binders such as starch pastes, including corn starch, wheat starch, rice starch, potato starch, gelatin, tragacanth, methyl cellulose, hydroxypropyl methyl cellulose, sodium carboxymethyl cellulose, or polyvinylpyrrolidone. If desired, disintegrating agents may be added, for example, starch as mentioned above, as well as carboxymethyl starch, crosslinked polyvinyl pyrrolidone, agar, or alginic acid or a salt thereof, such as sodium alginate. Adjuvants are in particular flow regulators and lubricants, for example, silica, talc, stearates, such as calcium magnesium stearate, stearic acid or polyethylene glycol. If necessary, a suitable coating that is resistant to gastric juice can be provided to the tablet core. For this purpose, concentrated sugar solutions can be used. This solution may contain gum arabic, talc, polyvinylpyrrolidone, polyethylene glycol and/or titanium dioxide, a lacquer solution and a suitable organic solvent or solvent mixture. To prepare a gastric juice-resistant coating, a suitable cellulose solution can be used, such as cellulose acetate phthalate or hydroxypropyl methylcellulose phthalate. Dyestuffs or pigments can be added to the coating of tablets or lozenge cores, for example, to identify or characterize a combination of active ingredient or dosages.

Specific administration methods include, but not limited to, various administration methods known in the art, which can be determined according to the actual situation of a patient. These methods include, but not limited to, parenteral, subcutaneous, intravenous, intramuscular, intraperitoneal, transdermal, oral, intrathecal, intracranial, nasal, or topical routes of administration.

Advantages of the Present Invention:

1. A series of saponin compounds capable of inhibiting PD-1 from binding to its ligand are, for the first time, discovered in the present invention;
2. The compounds of the present invention are natural products, and therefore have advantages of easy availability, low toxic and side effects;
3. The compounds of the present invention provide a new material basis for the development of PD-1, especially hPD-1 inhibitors.

The technical solution of the present invention will be further described below in combination with specific examples, however, the following examples do not constitute a limitation on the present invention. All the various application methods adopted in accordance with the principles and technical means of the present invention belong to the scope of the present invention.

The experimental methods without specific conditions in the following examples are generally based on conventional conditions or conditions recommended by the manufacturer. Unless otherwise stated, percentages and parts are by weight.

Example 1. Construction of PD-1 Expression Vector

A target gene was selected according to the related literature (amino acids 34-150 of human PD-1). Two restriction sites, NcoI and NdeI were used to clone the target gene into pET-28a vector. Firstly, specific primers were designed according to the NcoI and NdeI restriction sites to PCR amplify human PD-1 gene. Then the vector plasmid and PCR products were double-digested with two restriction enzymes, NcoI and NdeI, respectively by traditional cloning method, and then ligated to form a recombinant plasmid by using T4 ligase, and finally, the recombinant plasmid was transformed into E. coli DH5α competent cells. After cultured overnight, single clones were picked for identification.

Example 2. Expression and Purification of PD-1 Protein

Colonies with perfectly matched sequences after sequencing were selected and cultured overnight, the plasmid was extracted, and the plasmid was transformed into expression host E. coli BL21 (DE3) for expression. A single clone transformed to E. coli BL21 (DE3) was picked and placed in a 20 mL 2×YT medium containing kanamycin and cultured overnight in a shaker at 37° C. The next day, the culture was transferred to a TB medium containing kanamycin, cultured at 37° C. to OD600 of 0.6-0.8, and 0.5 mM IPTG was added for induction for 5-7 h at 37° C. The bacteria were collected by centrifugation at 4000 rpm, lysed with lysis buffer (50 mM Tris-HCl, pH 8.0, 50 mM NaCl, 1 mM DTT, 0.5 mM EDTA, 5% glycerol), then crushed under high pressure, and centrifuged at 12000 rpm for 60 min. The pellets were taken and washed with washing buffer (20 mM Tris-HCl, pH 8.0, 2M urea, 2.5% Triton X-100) for three times. The pellets were taken. Afterwards, a lysis buffer (20 mM Tris-HCl, pH 8.0, 8M urea) was used for dissolving the protein, the obtained system was centrifuged and the supernatant was taken. The protein supernatant was concentrated in a 3 kDa ultrafiltration tube to about 5 mL and added into 1 L of renaturing buffer (50 mM Tris-HCl, pH 8.0, 50 mM L-Arg, 24 mM NaCl, 1 mM KCl, 1 mM EDTA), renatured at 4° C. for 24 h by dilution method. And then, the protein solution was concentrated in a 3 kDa ultrafiltration tube to about 20 mL, loaded into a dialysis bag, and dialyzed overnight against dialysis buffer (50 mM Tris-HCl, pH 8.0, 150 mM NaCl, 1 mM DTT) for replace L-Arg in the renaturing buffer. The solution was concentrated and purified through cation exchange column and molecular sieve. After passed through the molecular sieve, the protein was subjected to 14% SDS-PAGE gel electrophoresis to identify the purity of the purified protein. The results are shown in FIG. 1. The molecular weight of the purified protein was about 13 kDa, which was consistent with the theoretically calculated molecular weight of the human PD-1 protein, and the protein purity was high.

Example 3. Identification of PD-1 Protein

Figure 2:
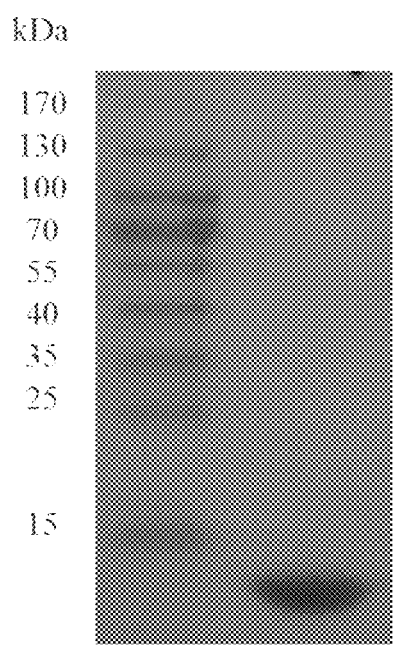
FIG. 2 shows the results of Western blot of purified human PD-1 from Example 3.
Figure 3A:
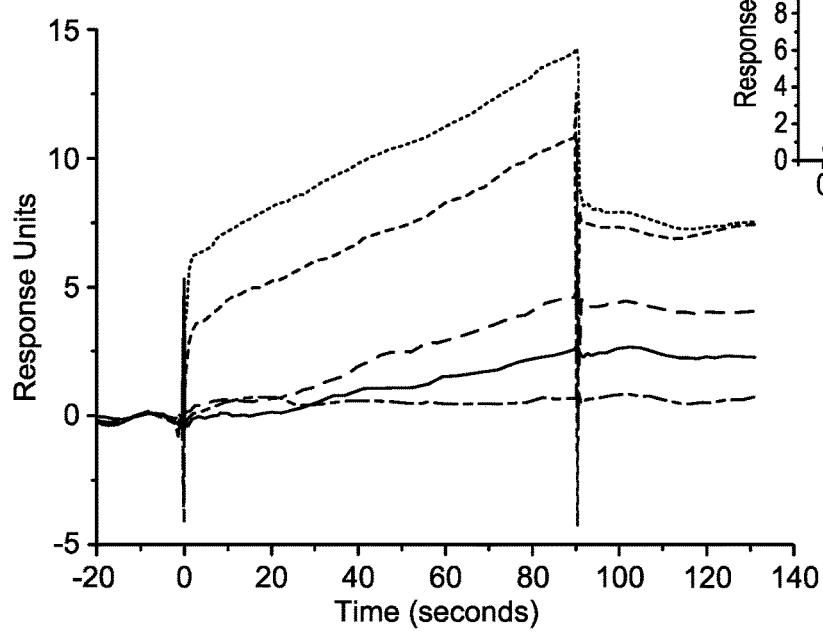
FIG. 3A-M shows SPR diagrams for determining the binding constants of compounds 1, 2, 3, 4, 5, 6, 7, 8, 9, 10, 11, 12, 13 to human PD-1 protein.
Figure 3B:
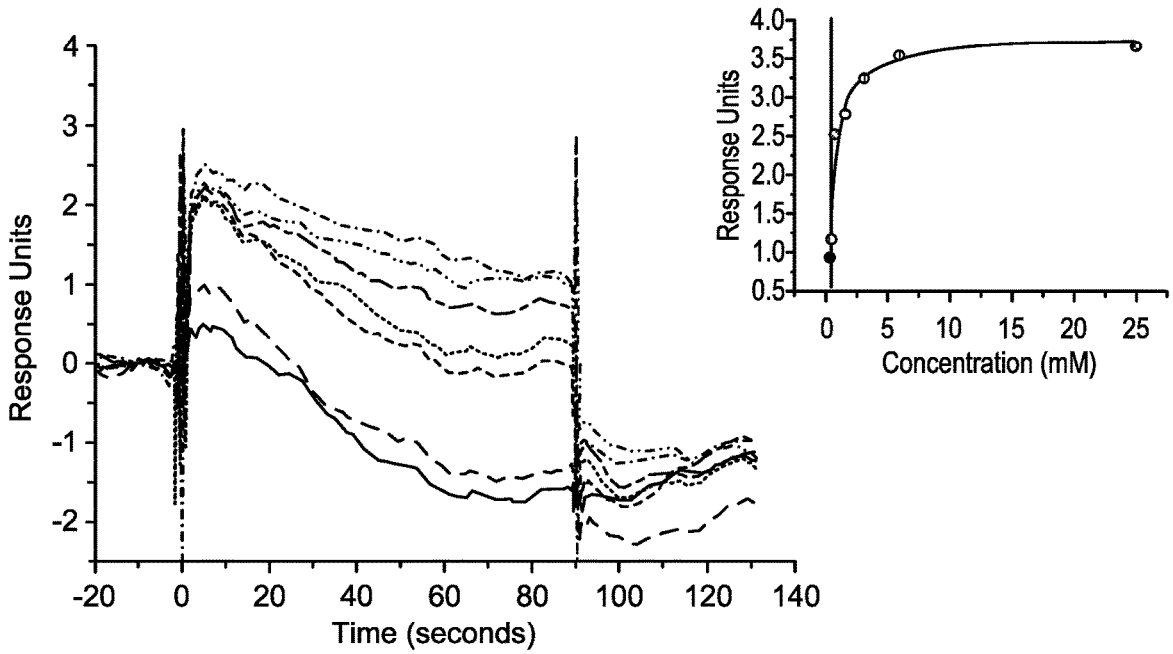
Figure 3C:
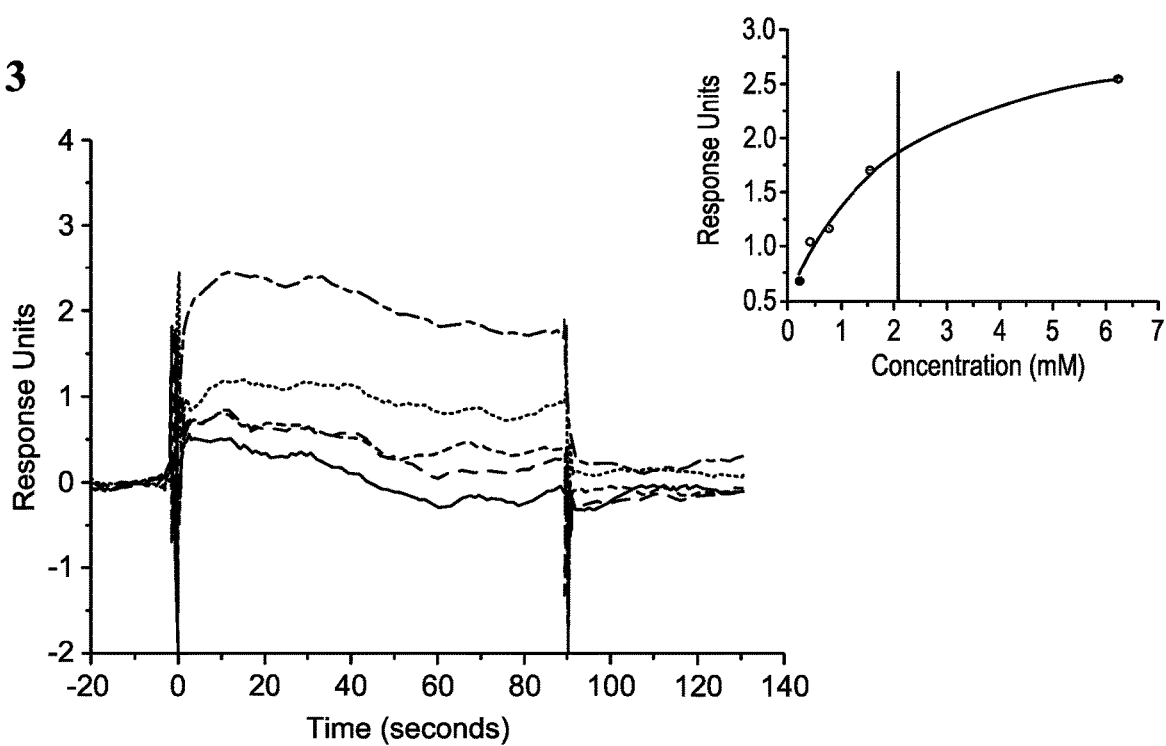
Figure 3D:
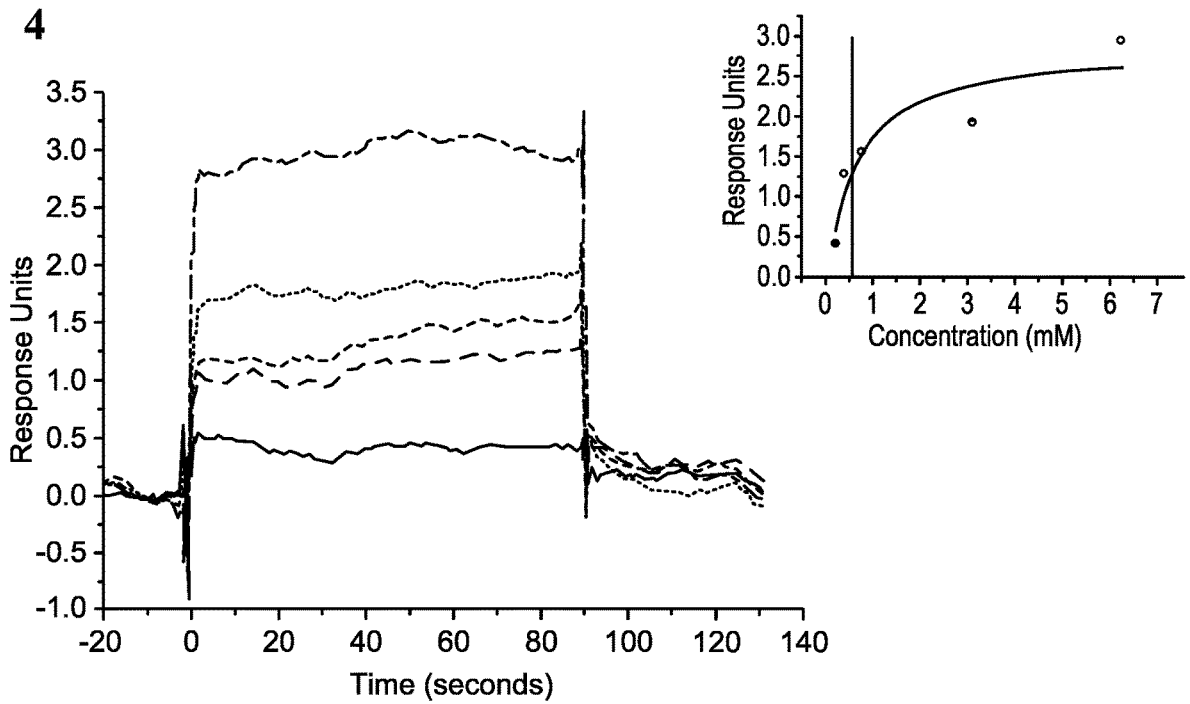
Figure 3E:
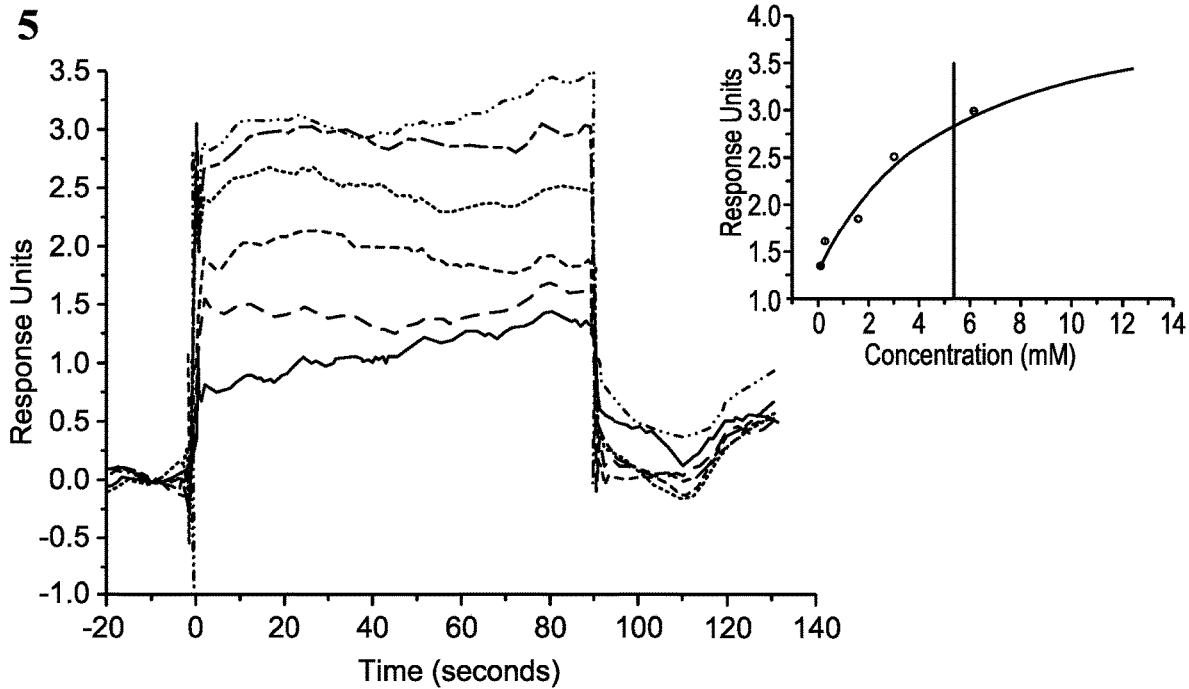
Figure 3F:
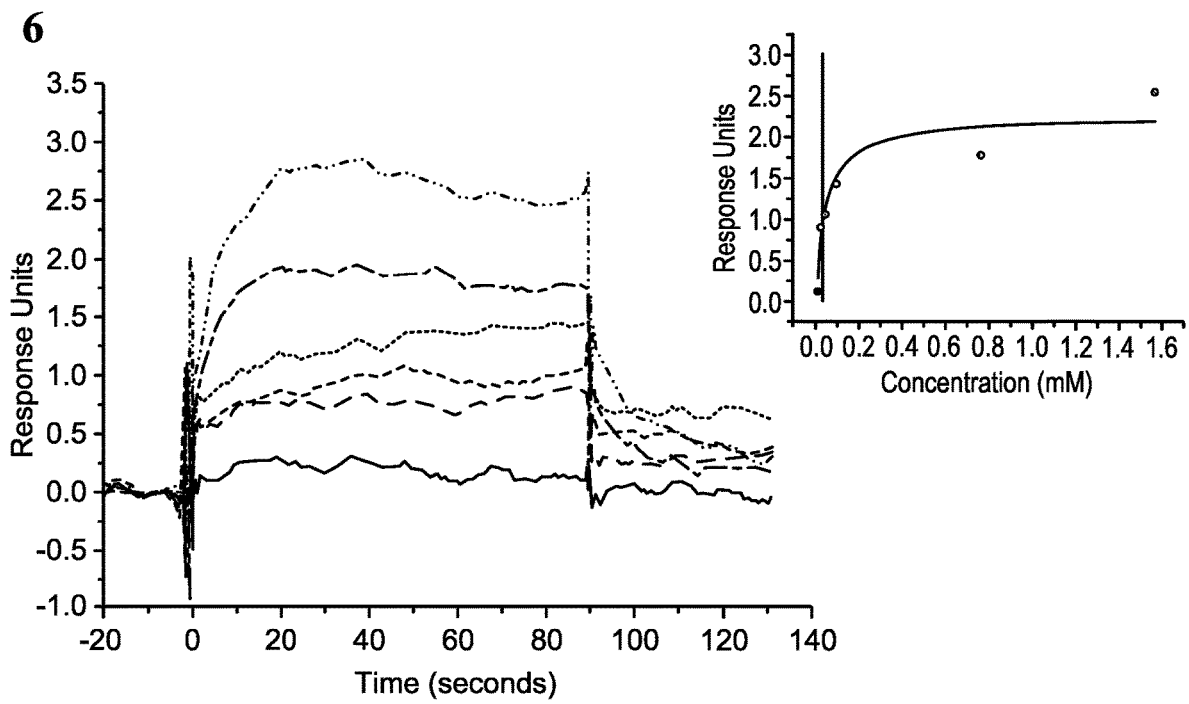
Figure 3G:
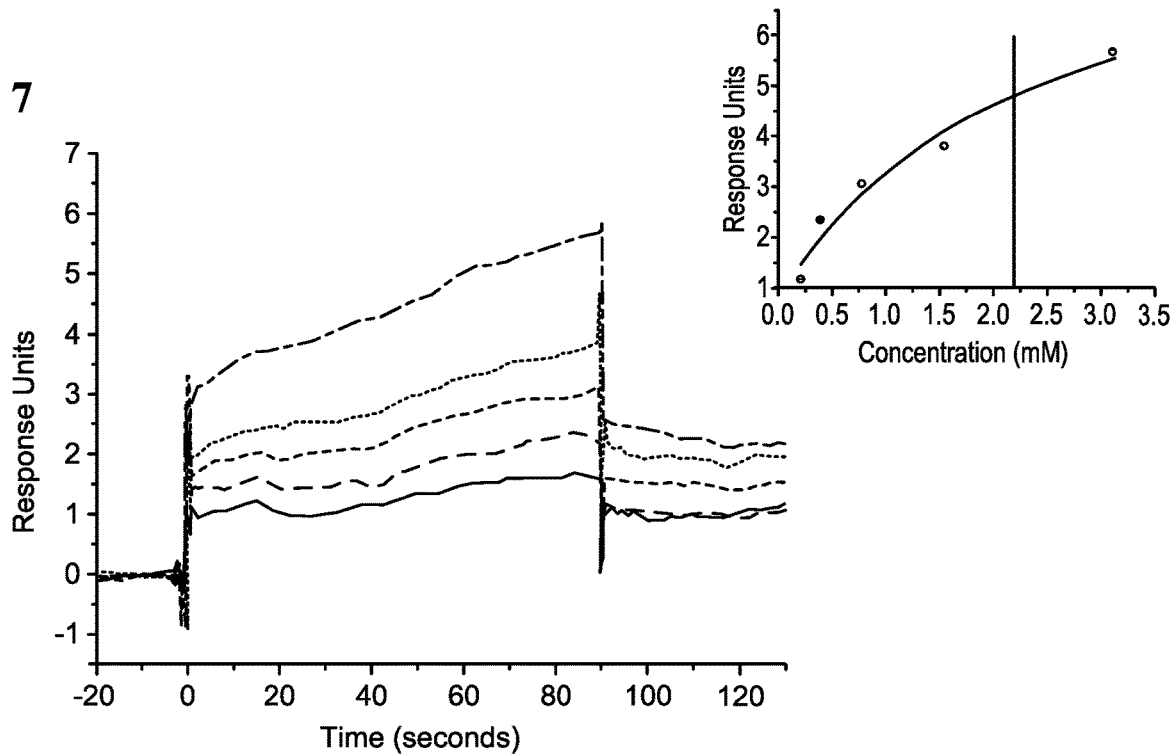
Figure 3H:
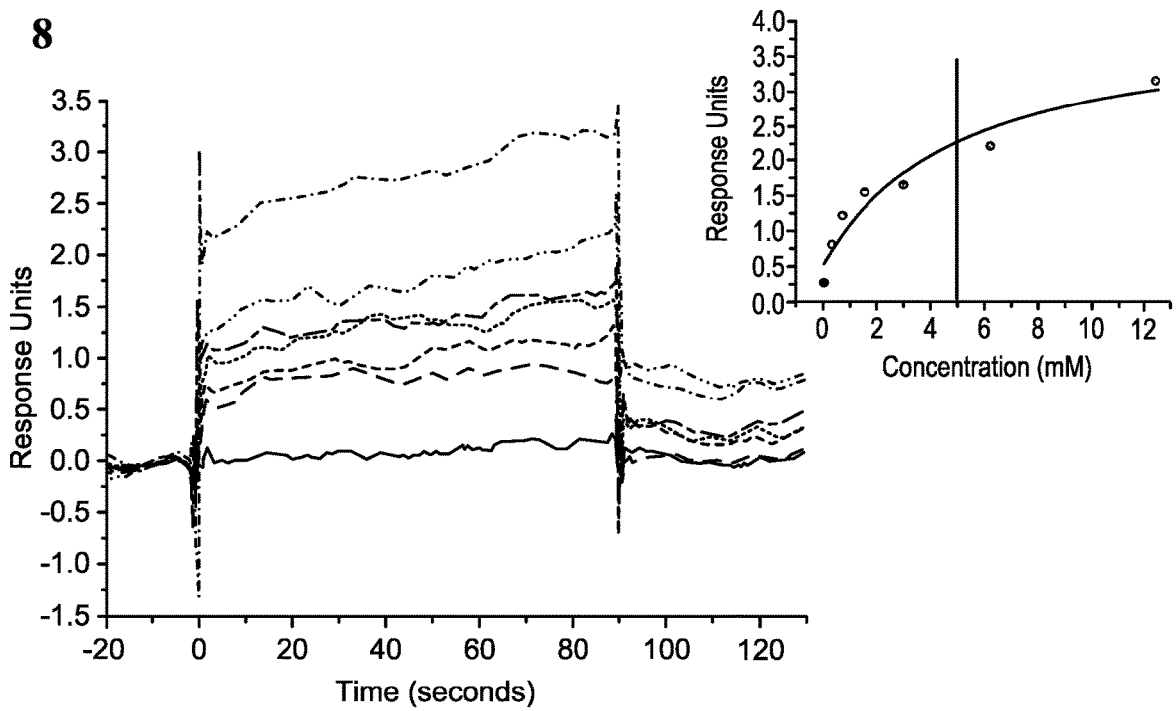
Figure 3I:
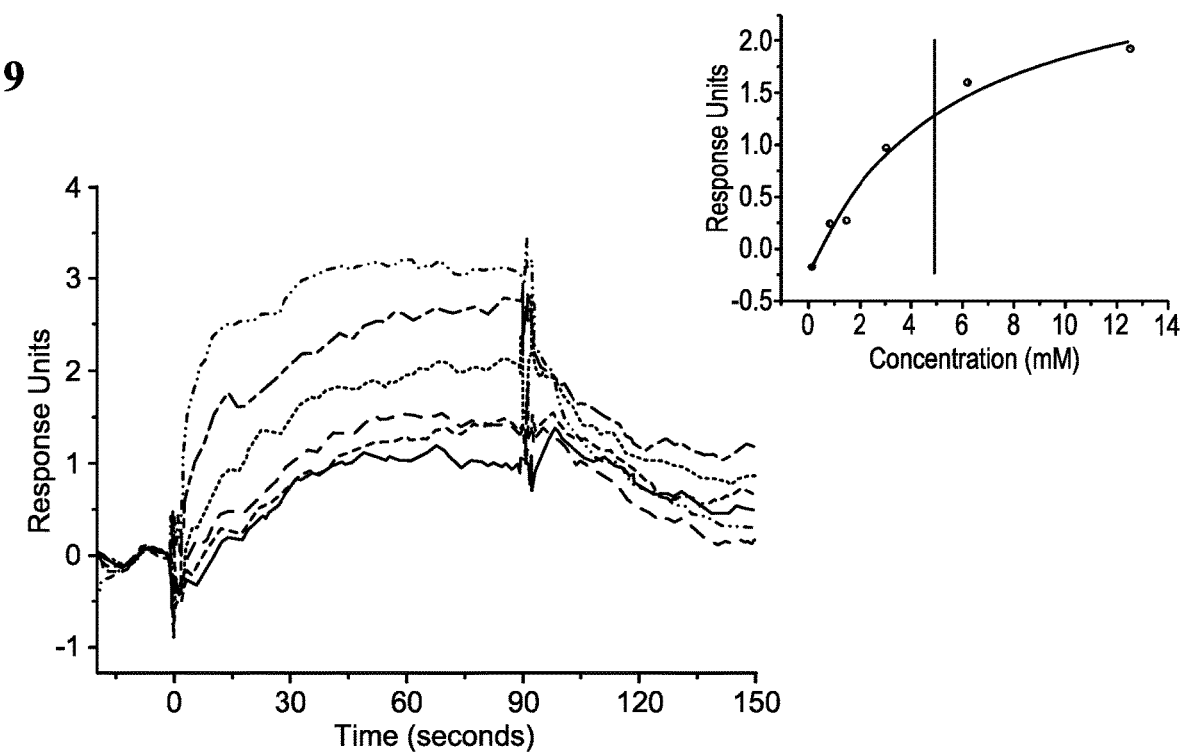
Figure 3J:
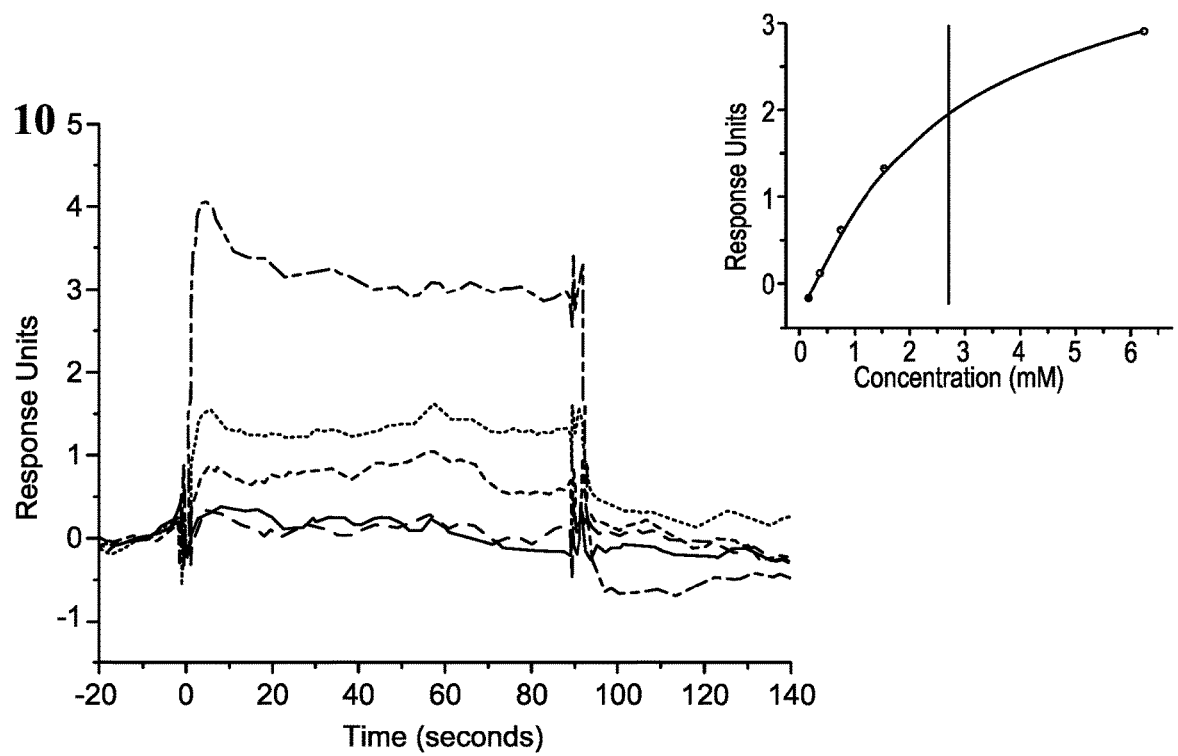
Figure 3K:
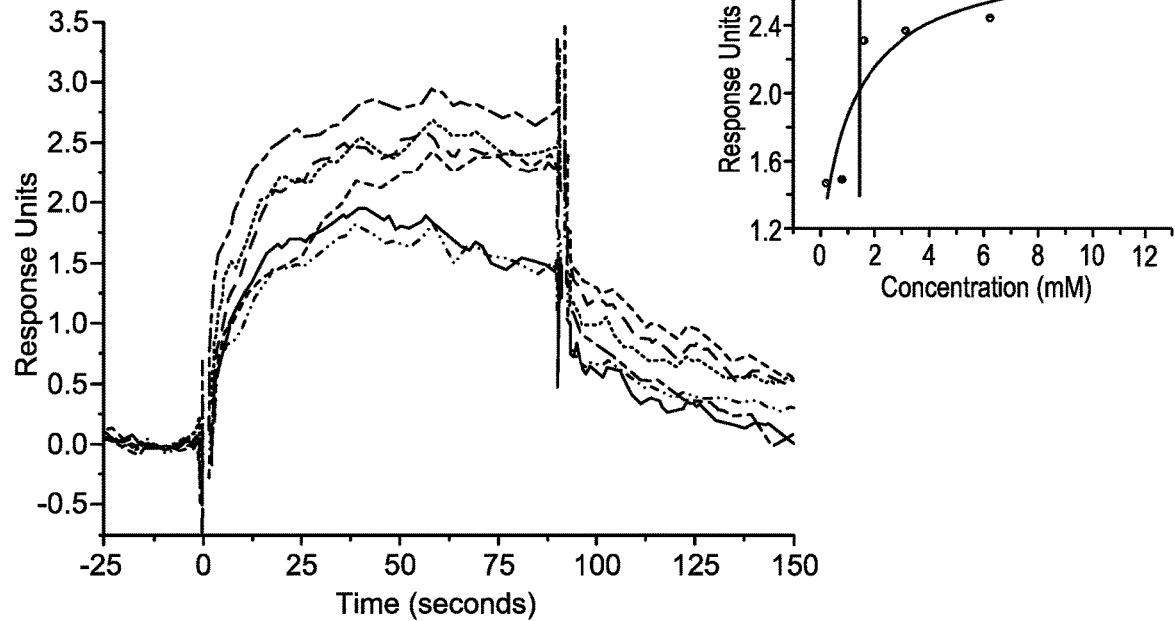
Figure 3L:
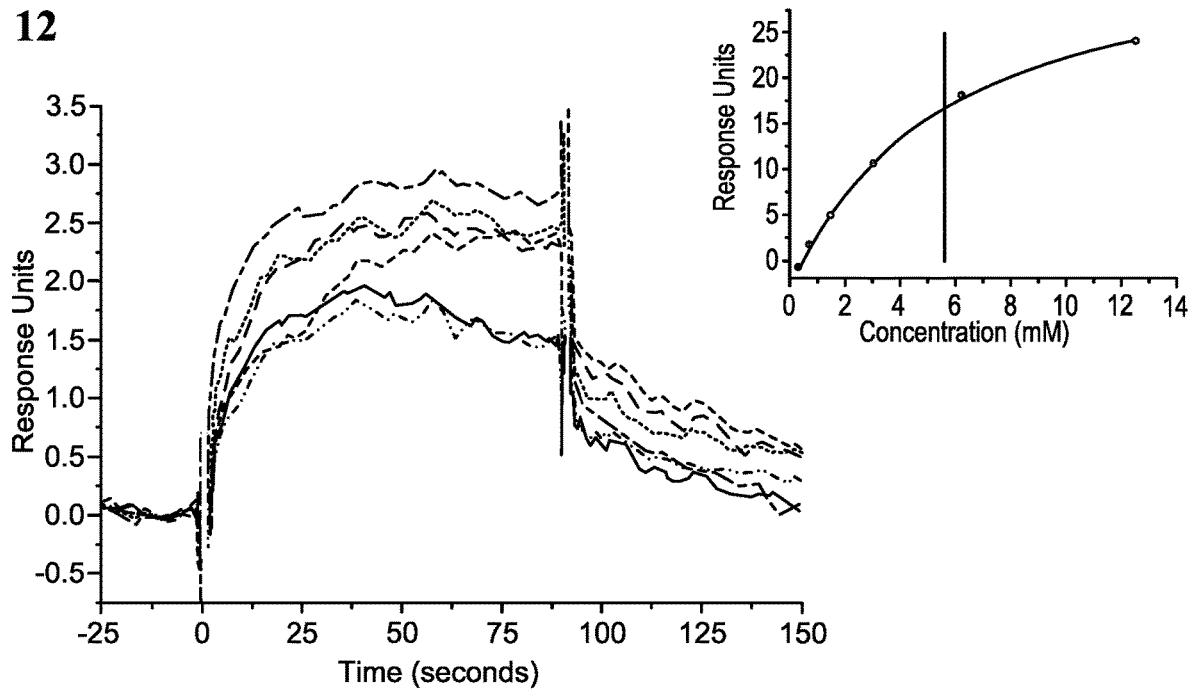
Figure 3M:
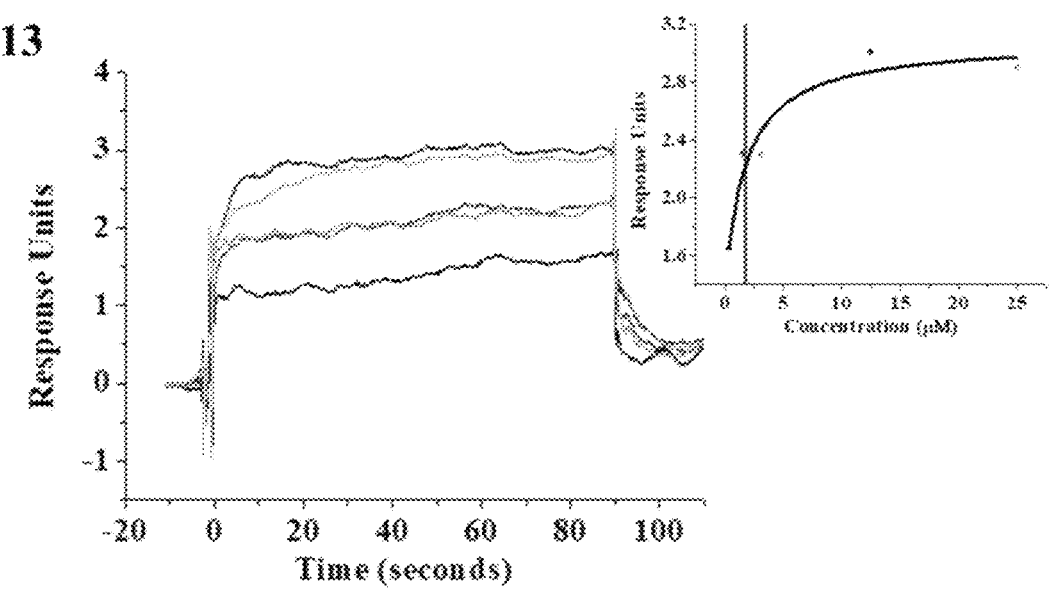
Figure 4A:
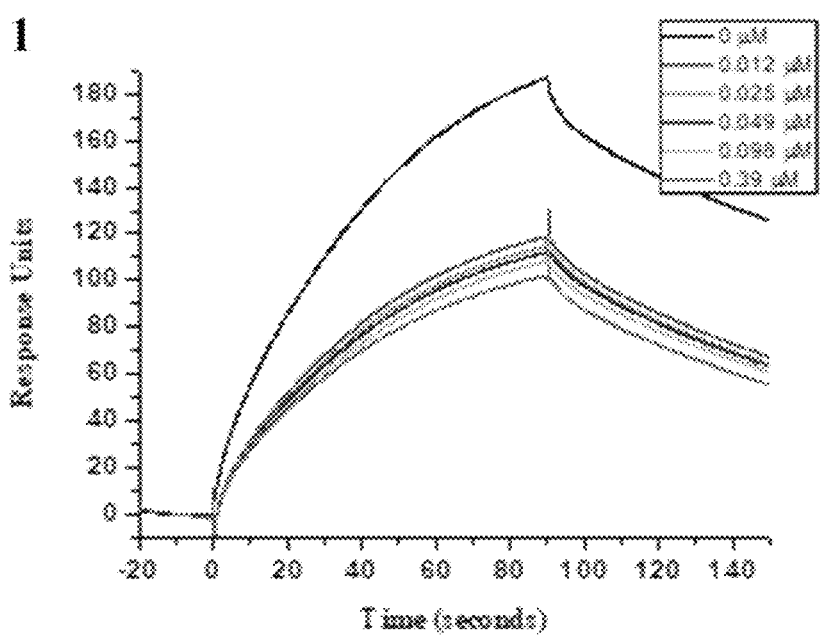
FIG. 4A-L shows SPR diagrams of compounds 1, 2, 4, 5, 6, 7, 8, 9, 10, 11, 12, 13, competiting with PD-L1 protein for binding to human PD-1 protein, showing that the compounds can block human PD-1 from binding to human PD-L1.
Figure 4B:
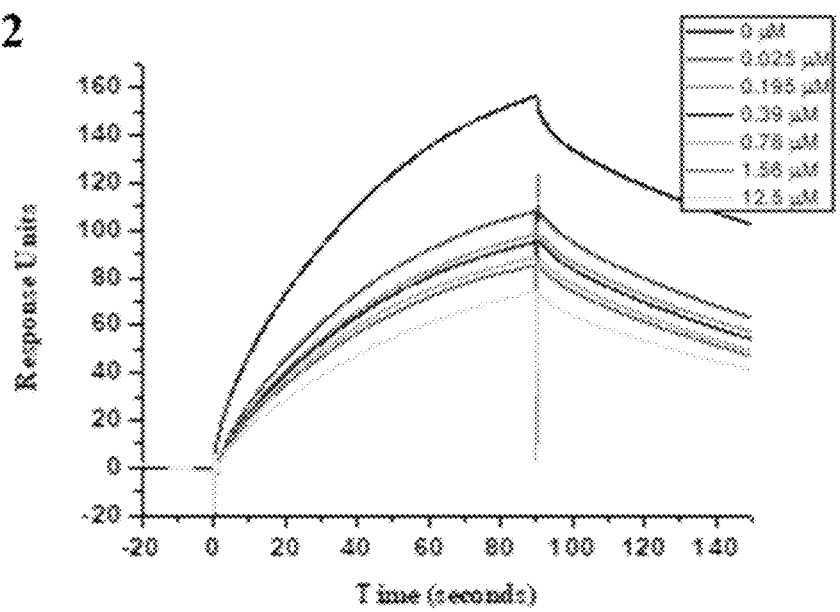
Figure 4C:
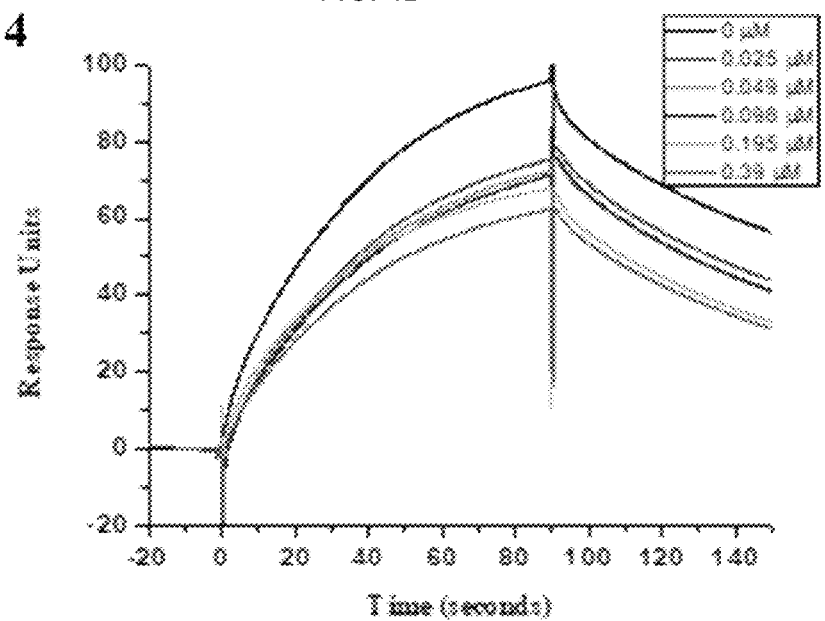
Figure 4D:
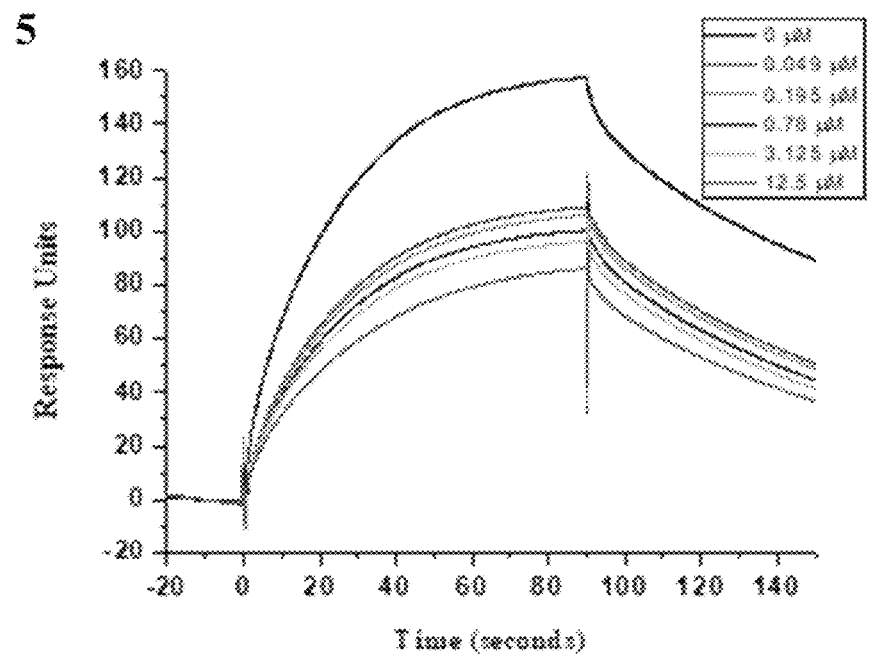
Figure 4E:
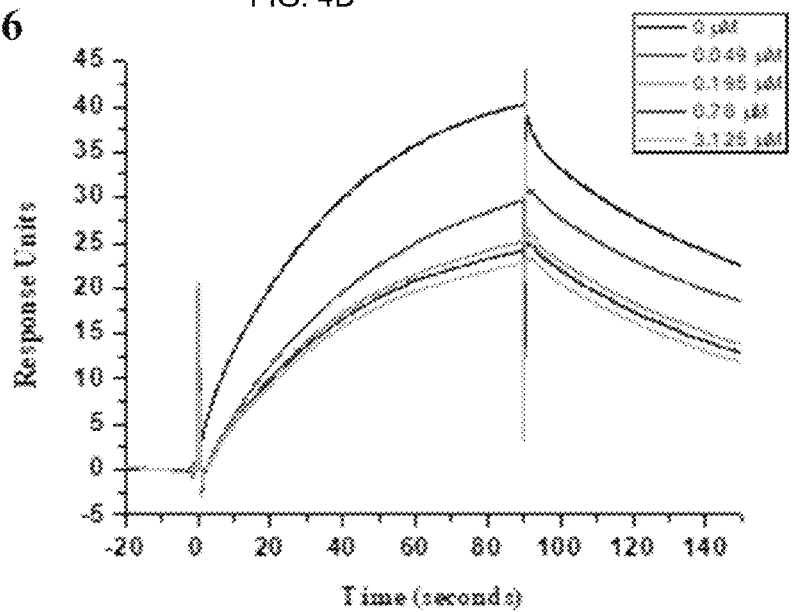
Figure 4F:
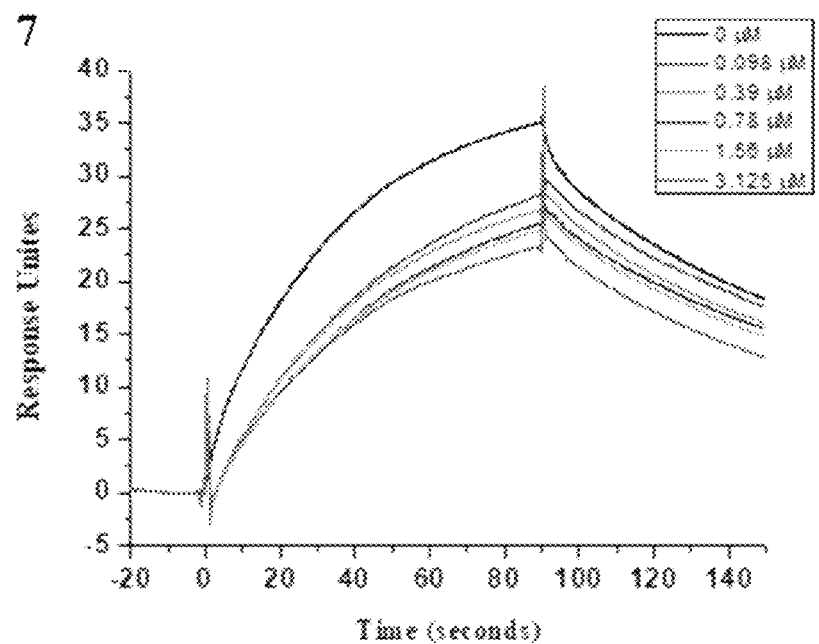
Figure 4G:
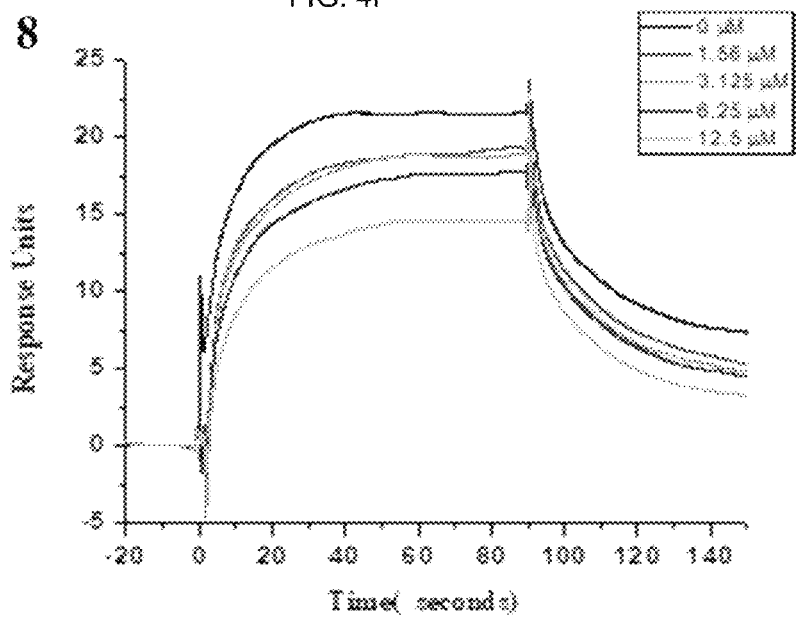
Figure 4H:
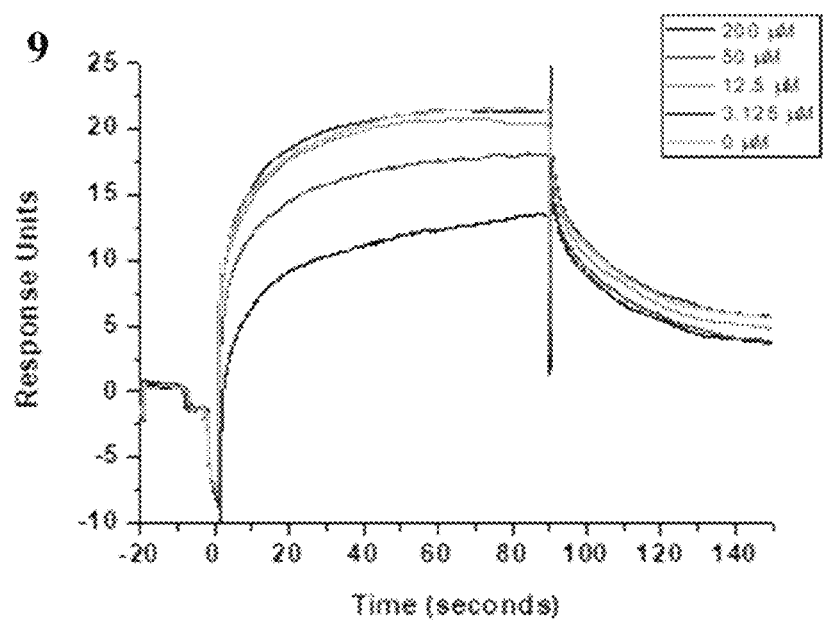
Figure 4I:
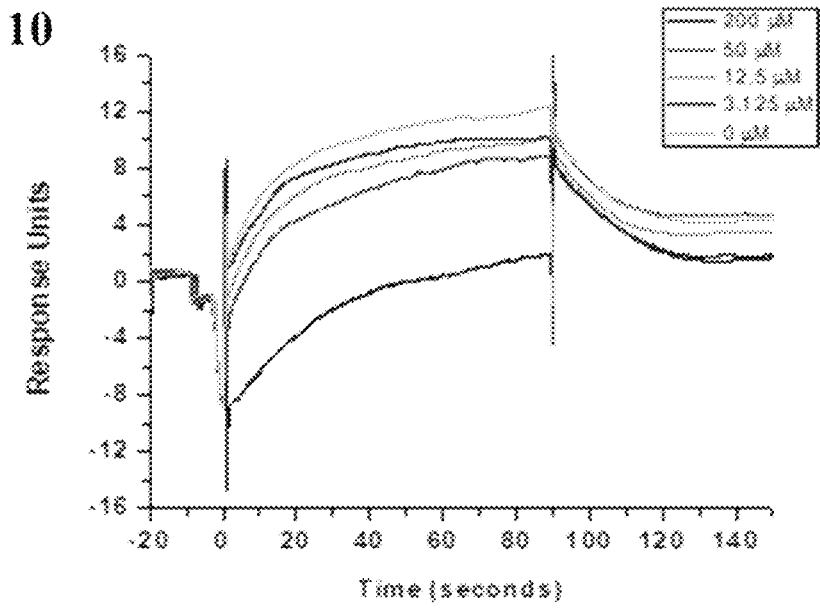
Figure 4J:
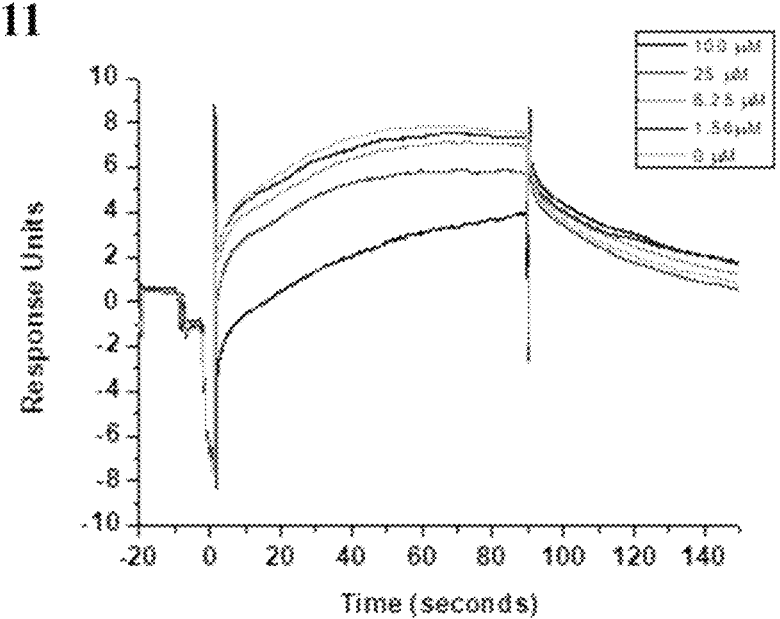
Figure 4K:
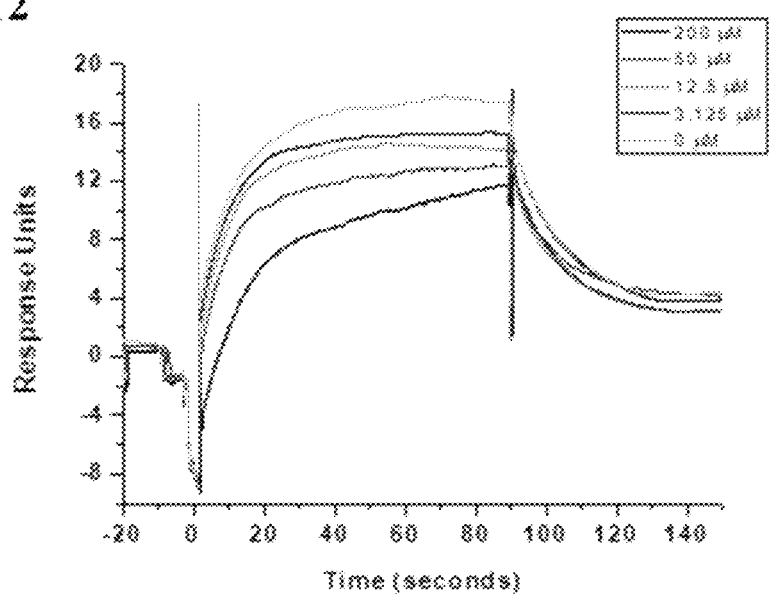
Figure 4L:
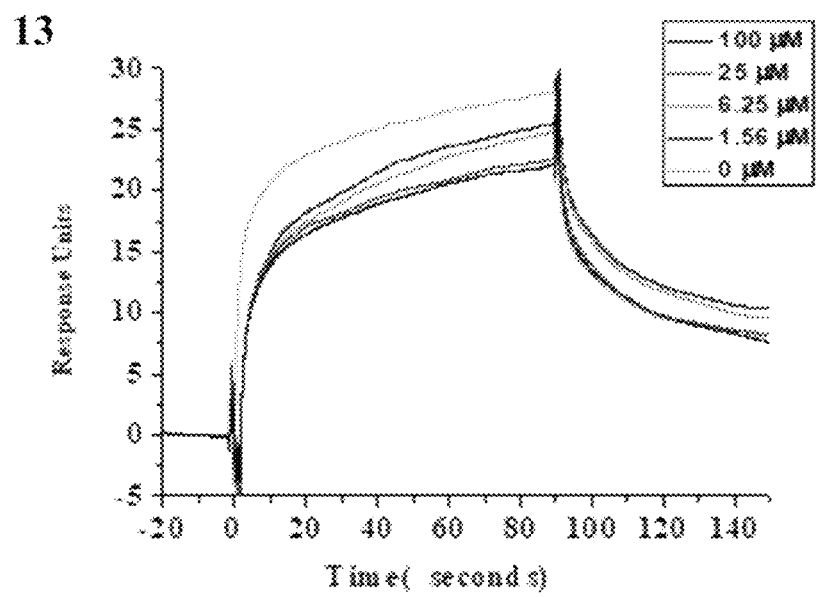
Figure 5A:
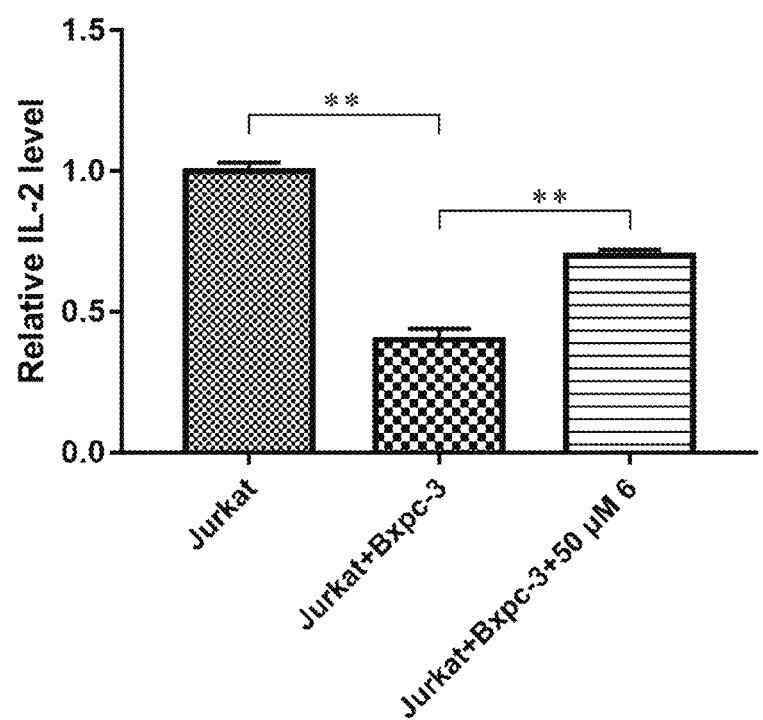
FIG. 5A-E shows that compounds 6, 8, 10, 11 and 13 can restore the ability of depleted Jurkat T cells to secrete IL-2, indicating that the compounds can, to a certain extent, restore the immune function of Jurkat T cells.
Figure 5B:
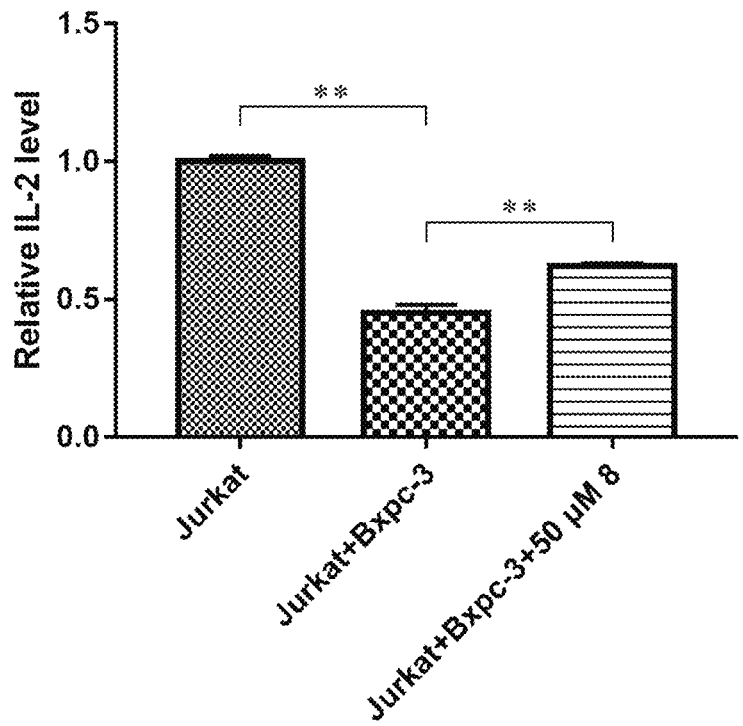
Figure 5C:
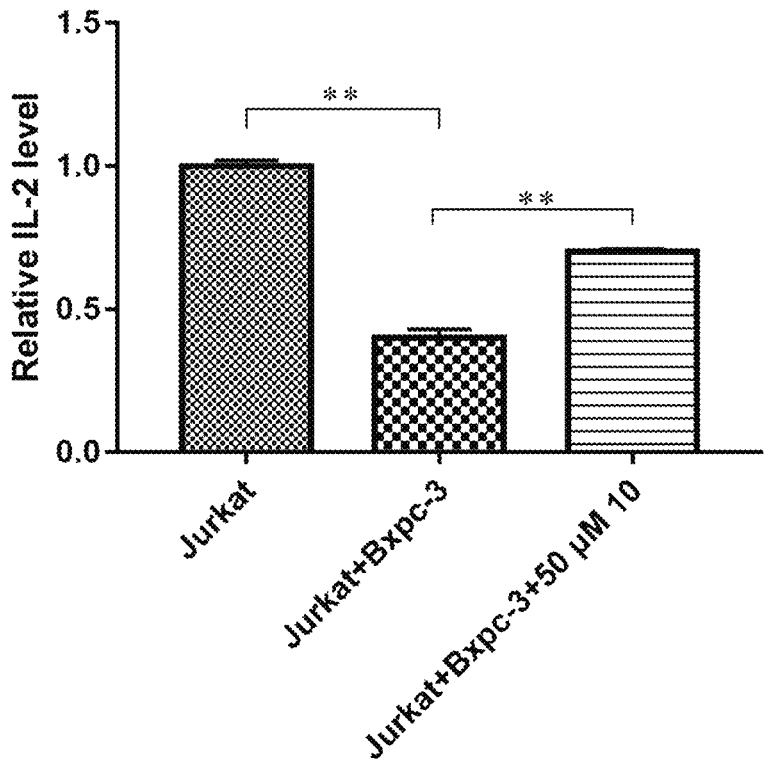
Figure 5D:
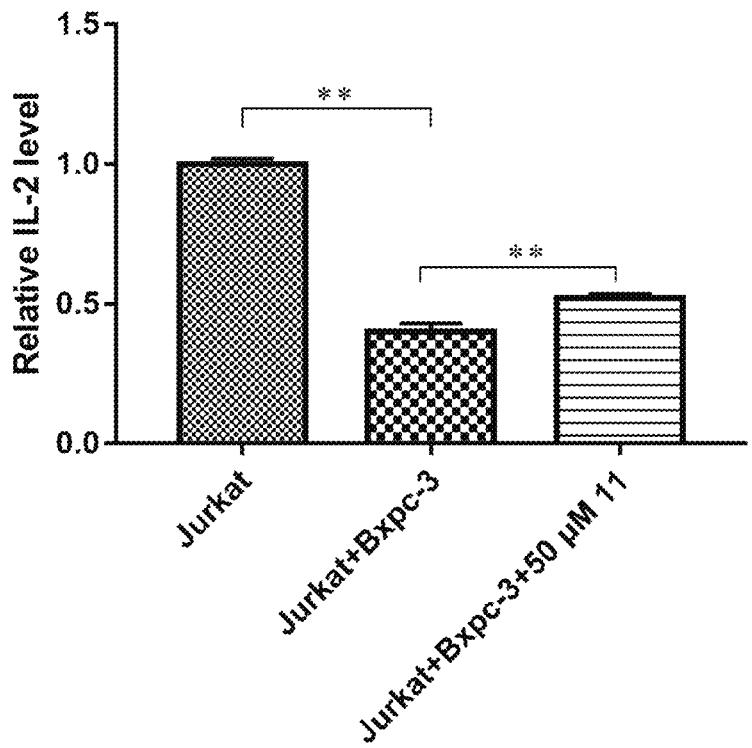
Figure 5E:
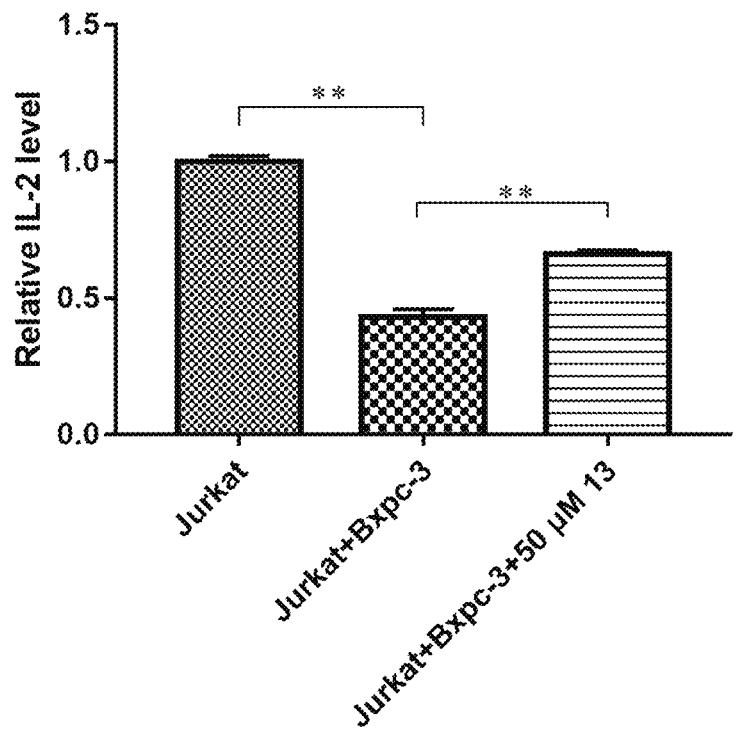

The purified PD-1 protein was subjected to 14% SDS-PAGE gel electrophoresis, and then transferred to a membrane at a transfer current of 300 mA and a transfer time of 45 min. The membrane was then blocked with 5% skimmed milk powder at room temperature for 2 h. The membrane was removed, incubated with mouse anti-human PD-1 monoclonal antibody at 4° C. overnight, rinsed for three times in 1×TBST solution, incubated with goat anti-mouse monoclonal antibody for 2 h at room temperature, and rinsed for three times in 1×TBST solution. A developing solution was added, and the membrane was developed in a fully automatic chemiluminescence image analysis system. The result is shown in FIG. 2. A protein band can be found between 10-15 kDa and can be developed by using PD-1 antibody, which shows that the purified protein is indeed human PD-1 protein.

Example 4. Determination of Binding Constants Between Saponin Natural Products and PD-1 Protein by SPR The natural products used in the examples were purchased from Baoji Chenguang Biological Co., Ltd.

Surface plasmon resonance (SPR) was used to determine the binding affinity between natural products and PD-1 protein. Specific experimental steps are as follows: Firstly, the purified protein was exchanged into 50 mM Hepes, pH 8.0, 250 mM NaCl, 1 mM DTT buffer, and diluted to 50 μg/ml with sodium acetate pH 4.5. The protein was coupled to CM7 chip with a coupling kit for 600 s at a flow rate of 10 μl/min. The final coupling amount was about 13000 RU. After the coupling was completed, the CM7 chip was equilibrated to a stable state in a buffer solution (1.05×PBS, 0.05% P20). Then the compound was diluted to a series of different concentrations with a running buffer (1.05×PBS, 0.05% P20, 1% DMSO), and flowed across the surface of the chip along with the running buffer at a flow rate of 30 μL/min, for binding time of 90 s and dissociation time of 120 s. The final data was analyzed by BIAevaluation2.0 software, and KD values were obtained by steady-state fitting. The KD values of the tested compounds are listed in Table 1 below.

TABLE 1

Binding affinity KD value between the small molecule compound of the present invention and recombinant human PD-1 protein

| Id | $K_D$ (μM) |
|---|---|
| 1 | 2.23 |
| 2 | 0.44 |
| 3 | 2.10 |
| 4 | 0.56 |
| 5 | 5.36 |
| 6 | 0.04 |
| 7 | 2.19 |
| 8 | 5.02 |
| 9 | 4.92 |
| 10 | 2.71 |
| 11 | 1.40 |
| 12 | 5.62 |
| 13 | 1.77 |

Example 5. SPR Experiment of PD-L1 Protein Competiting with Saponin Natural Products for Binding PD-1

Based on the results in the above examples, the present inventors investigated whether the compound can competite with PD-L1 for binding PD-1, and thus block PD-1 from binding PD-L1. PD-L1 protein was purchased from Beijing Yiqiao Shenzhou Biotechnology Co., Ltd. Specific experimental steps are as follows: 50 μg/ml PD-L1 protein was coupled to CM5 chip by amino coupling method. The coupling amount was about 3780 RU. Compounds of different concentrations were incubated with 3 μM PD-1 protein on ice for 30 min, and flowed across the surface of the chip along with the running buffer (1.05×PBS, 0.05% P20, 1% DMSO) at a flow rate of 30 μL/min, for binding time of 90 s and dissociation time of 120 s. The final data was analyzed by BIAevaluation2.0 software, and the results are shown in FIG. 3. PD-1 protein bound to PD-L1 protein on the chip decreases as the concentration of the compound increases, therefore, the response value decreases. The results of this experiment indicate that compounds can block PD-1 from binding PD-L1.

Example. Detection of IL-2 Secretion in T Cells by ELISA

The inventors selected several compounds for the evaluation experiment of cell function. We co-cultured stimulated BxPC-3 tumor cells and activated Jurkat T cells in a 96-well plate at a ratio of 3:1. Jurkat T cells were cultured alone as a negative control. 50 μM of compound was added into the experimental group, and a D-hank's solution with the same DMSO content was used as a negative control. Each group was incubated in a carbon dioxide cell incubator for 48 h. The supernatant medium was collected and detected for the amount of IL-2 by an ELISA kit. Experiments were performed in triplicate. The results are shown in FIG. 4. After tumor cells were co-cultured with T cells, the amount of IL-2 produced by the T cells was suppressed by about 55%. After 50 μM of compound 6 was added, the amount of IL-2 produced by Jurkat T cells can be increased by about 30%; after 50 μM of compound 8 was added, the amount of IL-2 produced by Jurkat T cells can be increased by about $1^7$%; after 50 μM of compound 10 was added, the amount of IL-2 produced by Jurkat T cells can be increased by about 30%; after 50 μM of compound 11 was added, the amount of IL-2 produced by Jurkat T cells can be increased by about 12%; and after 50 μM of compound 13 was added, the amount of IL-2 produced by Jurkat T cells can be increased by about 23%. Such effects can be achieved in three repeated experiments. The results of this experiment indicate that the compounds can, to a certain extent, restore the function of T cells.

Discussion: The compound of the present invention and natural products of saponin can bind PD-1 protein, and at the same time, block PD-1 from binding PD-L1. And in the ELISA experiment, it was found that the compounds can, to a certain extent, restore the level of IL-2 secreted by Jurkat T cells, that is, to a certain extent, restore the function of Jurkat T cells.

All documents mentioned in the present invention are incorporated by reference in this application, as if each document was individually incorporated by reference. In addition, it should be understood that after reading the above teachings of the present invention, a skilled person can make various changes or modifications to the present invention, and these equivalent forms also fall within the scope defined by the claims appended to this application.

The invention claimed is:

1. A method for inhibiting PD-1 from binding PD-L1, comprising the steps of using a saponin compound or a pharmaceutically acceptable salt, prodrug, solvate thereof, or a pharmaceutical composition comprising said saponin compound to inhibit PD-1 from binding to PD-L1, wherein the saponin compound is represented by Formula I or II:

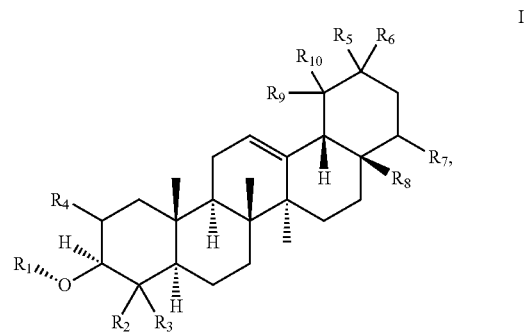

-continued

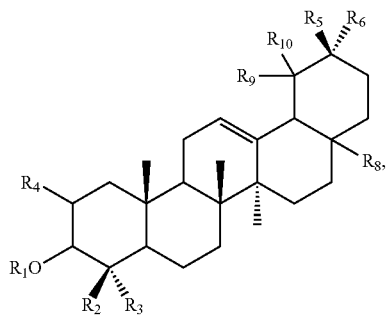

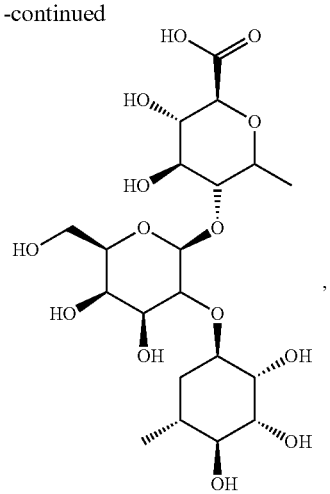

wherein, in Formula I,

R₁ is selected form the group consisting of:

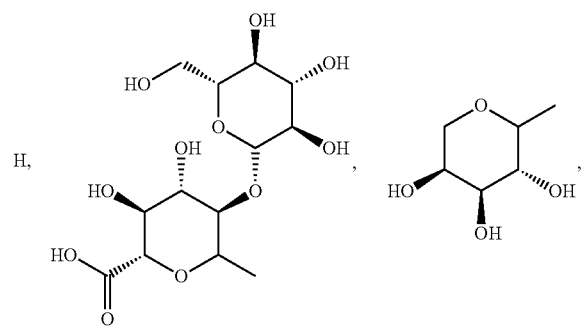

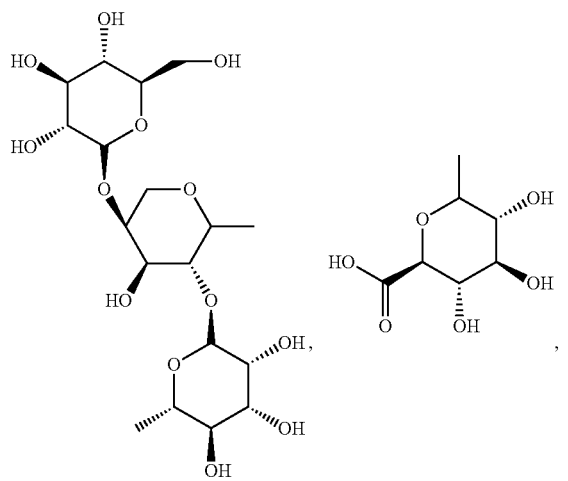

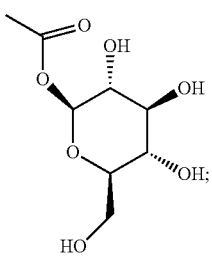

and $R_2$ and $R_3$ are each independently selected from the group consisting of: H, a substituted or unsubstituted $C_{1-3}$ alkyl, OH, and substituted or unsubstituted $C_{1-3}$ alkylenehydroxy;

$R_4$ is selected from the group consisting of: H, OH, a substituted or unsubstituted $C_{1-6}$ alkoxy, and —OC(O)$R_{11}$, wherein $R_{11}$ is hydrogen or a substituted or unsubstituted $C_{1-6}$ alkyl, preferably H or a substituted or unsubstituted $C_{1-3}$ alkyl;

$R_5$ and $R_6$ are each independently selected from the group consisting of: H and a substituted or unsubstituted $C_{1-3}$ alkyl;

$R_7$ is selected from the group consisting of: H and OH;

$R_8$ is selected from the group consisting of: H, —COOH, and and $R_9$ and $R_{10}$ are each independently selected from the group consisting of: H, a substituted or unsubstituted $C_{1-3}$ alkyl, and OH, and wherein Formula II is represented by the formula:

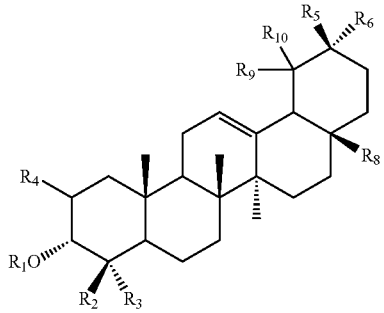

$R_1$ is selected form the group consisting of: H,

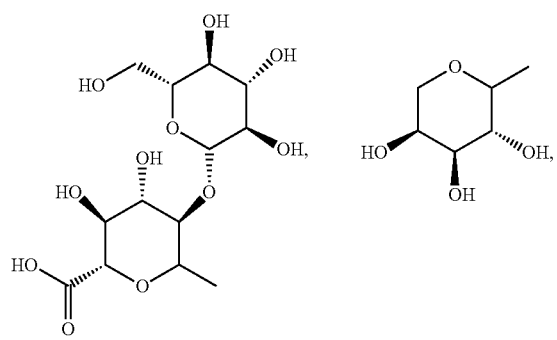

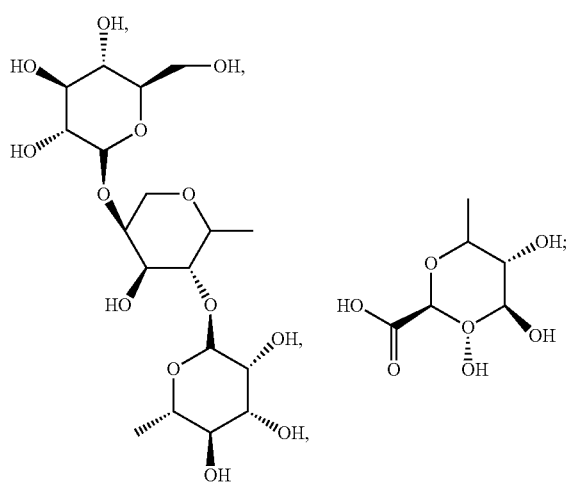

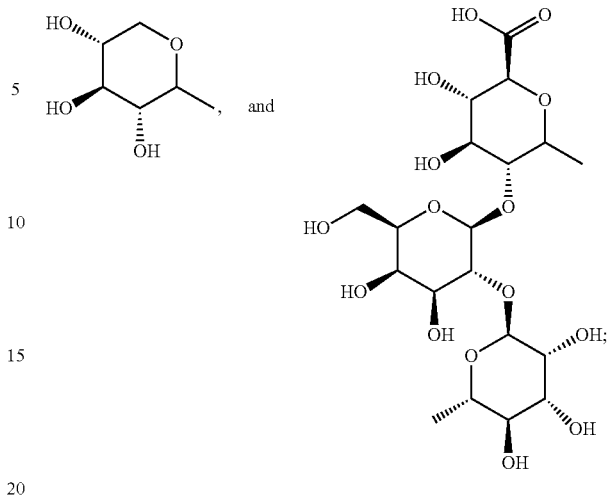

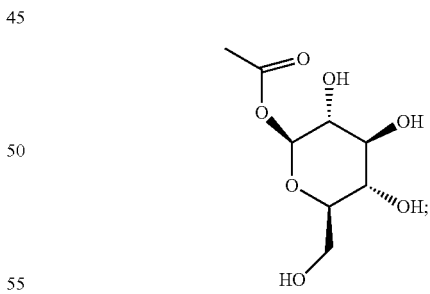

and $R_2$ and $R_3$ are each independently selected from the group consisting of: H, a substituted or unsubstituted $C_{1-6}$ alkyl, OH, and substituted or unsubstituted $C_{1-6}$ alkylenehydroxy;

$R_4$ is selected from the group consisting of: H, OH, a substituted or unsubstituted $C_{1-6}$ alkoxy, and —OC(O)$R_{11}$, wherein $R_{11}$ is hydrogen or a substituted or unsubstituted $C_{1-6}$ alkyl, preferably H or a substituted or unsubstituted $C_{1-3}$ alkyl;

$R_5$ and $R_6$ are each independently selected from the group consisting of: H and a substituted or unsubstituted $C_{1-6}$ alkyl;

$R_8$ is selected from the group consisting of: H, a $C_{1-3}$ carboxyl, substituted or unsubstituted $C_{2-7}$ ester group, and $R_9$ and $R_{10}$ are each independently selected from the group consisting of: H, a substituted or unsubstituted $C_{1-6}$ alkyl, and OH.

2. The method of claim 1, wherein the compound of Formula I or II is selected from the group consisting of:

| No. | Structure |
|---|---|
| 1 | 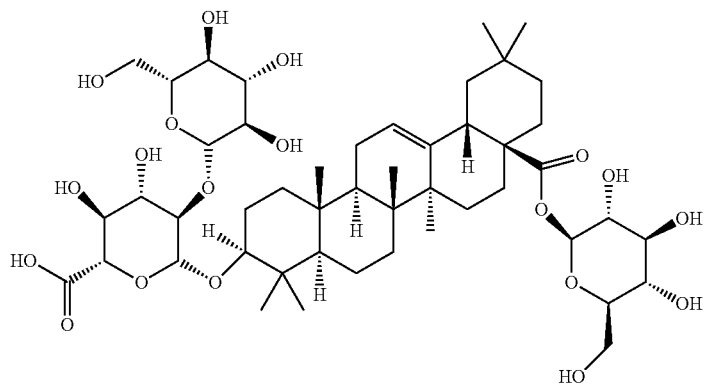 |
| 2 | 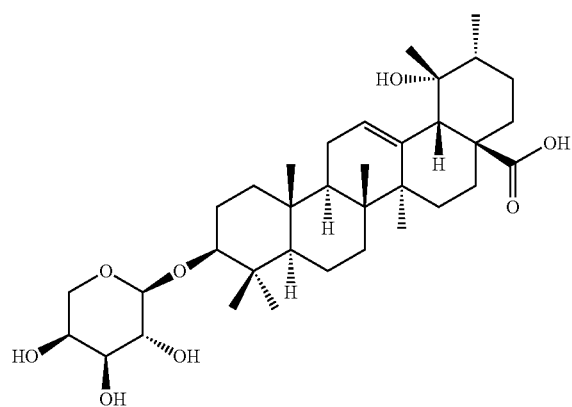 |
| 3 | 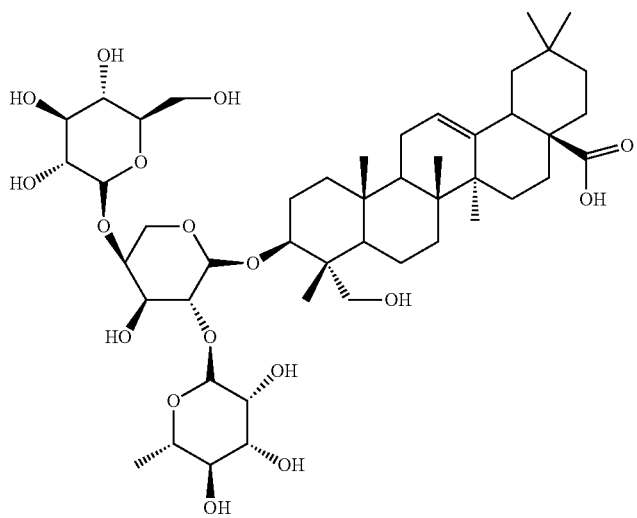 |

-continued
| No. | Structure |
|---|---|
| 4 | 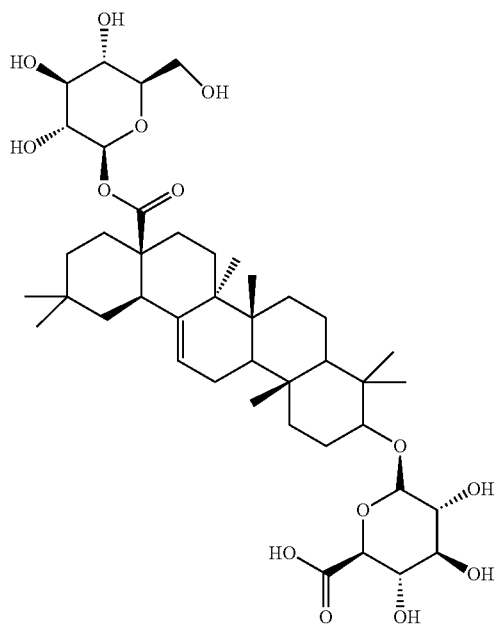 |
| 5 | 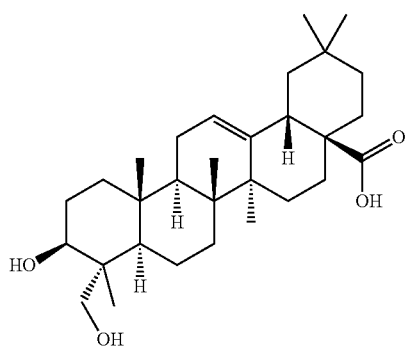 |
| 6 | 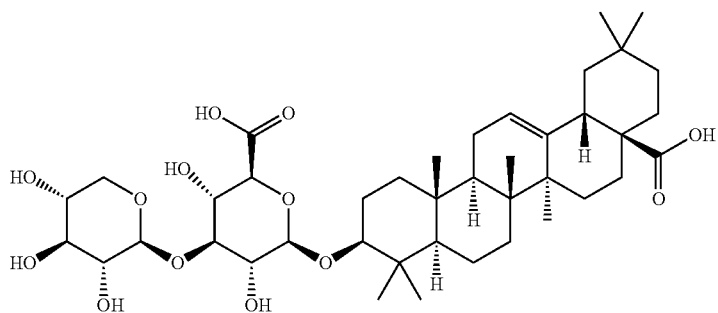 |

| No. | Structure |
|---|---|
| 7 | 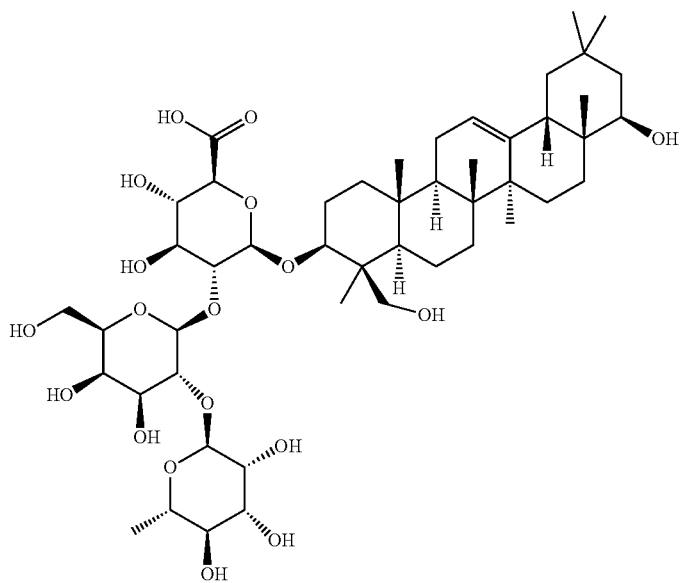 |
| 8 | 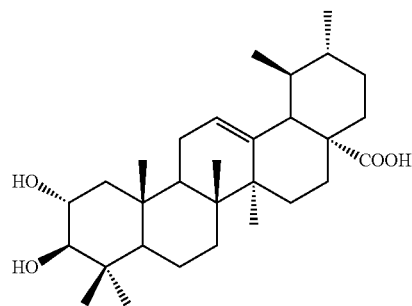 |
| 9. | 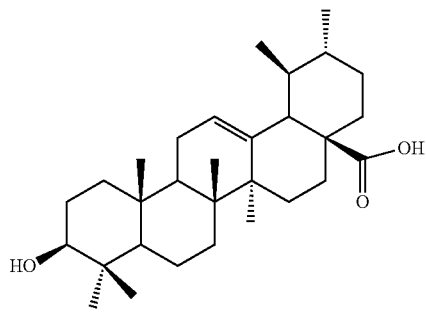
Ursolic acid (UA, 2) |
| 10 | 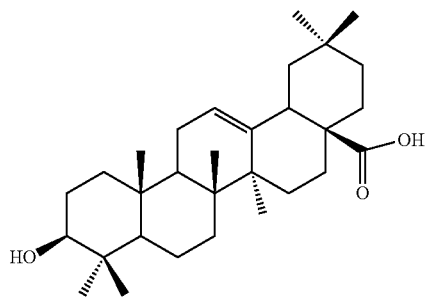
Oleanolic acid (OA, 1) |

-continued
| No. | Structure |
|---|---|
| 11 | 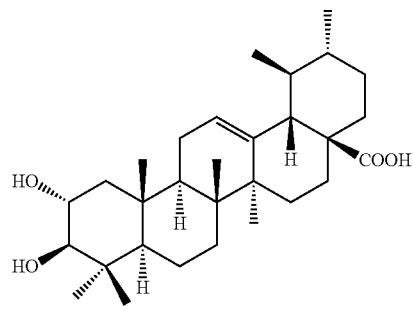 |
| 12 | 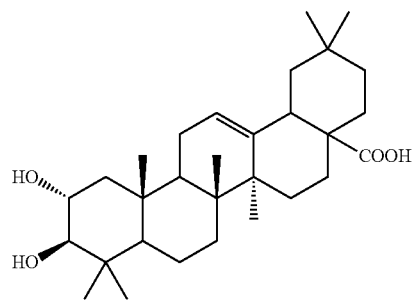 |
| 13 | 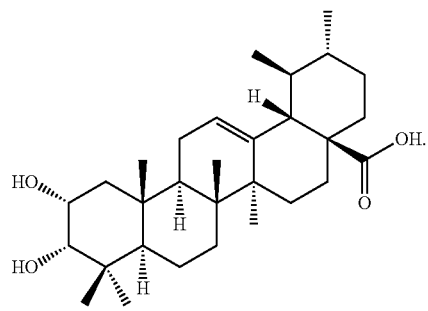 |
* * * * *